(12) United States Patent
Byron et al.

(10) Patent No.: US 7,128,067 B2
(45) Date of Patent: Oct. 31, 2006

(54) METHOD AND APPARATUS FOR GENERATING AN AEROSOL

(75) Inventors: Peter R. Byron, Richmond, VA (US); Michael Hindle, Glen Allen, VA (US)

(73) Assignee: Philip Morris USA Inc., Richmond, VA (US)

(*) Notice: Subject to any disclaimer, the term of this patent is extended or adjusted under 35 U.S.C. 154(b) by 123 days.

(21) Appl. No.: 10/394,654

(22) Filed: Mar. 24, 2003

(65) Prior Publication Data

US 2004/0016427 A1   Jan. 29, 2004

Related U.S. Application Data

(63) Continuation of application No. 09/560,510, filed on Apr. 27, 2000, now abandoned.

(51) Int. Cl.
*A61M 15/00* (2006.01)
*H05B 3/00* (2006.01)
*B67D 5/62* (2006.01)

(52) U.S. Cl. ............ 128/200.14; 128/203.17; 128/204.17; 516/8; 222/146.3

(58) Field of Classification Search .................. 128/200.14–200.24, 203.12, 203.14, 203.21, 128/203.17, 203.23, 203.27, 203.26, 204.17, 128/204.21, 204.23, 207.14, 207.18
See application file for complete search history.

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |
| 3,200,535 A | 8/1965 | Hession, Jr. et al. |
| 3,431,393 A | 3/1969 | Katsuda |
| 3,486,663 A | 12/1969 | Humphrey |
| 3,658,059 A | 4/1972 | Steil |
| 3,731,876 A | 5/1973 | Showalter |
| 3,750,961 A | 8/1973 | Franz |
| 3,847,304 A | 11/1974 | Cohen |
| 3,859,398 A | 1/1975 | Havstad |

(Continued)

FOREIGN PATENT DOCUMENTS

BE    354004 A    9/1928

(Continued)

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477-7505, May-Jun. 1994.

(Continued)

*Primary Examiner*—Glenn K. Dawson
(74) *Attorney, Agent, or Firm*—Buchanan Ingersoll & Rooney PC

(57) ABSTRACT

An aerosol is formed by supplying a material in liquid form to a flow passage and heating the flow passage such that the material volatizes and expands out of an open end of the flow passage. The volatized material combines with ambient air such that volatized material condenses to form the aerosol. An apparatus and method for generating such an aerosol are disclosed wherein the apparatus may include an electrically conductive sleeve at an open end of the flow passage, an electrically conductive flow passage and/or a spacer chamber. The volatilized material may contain a volatilized solute and vehicle such that the resulting aerosol particle sizes of the solute and the vehicle are either different or the same.

13 Claims, 12 Drawing Sheets

U.S. PATENT DOCUMENTS

| | | |
|---|---|---|
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A * | 5/1990 | Brooks et al. ......... 128/203.26 |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,007,419 A * | 4/1991 | Weinstein et al. ..... 128/200.23 |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,509,404 A * | 4/1996 | Lloyd et al. ........... 128/200.14 |
| 5,509,557 A | 4/1996 | Jimarez et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,674,860 A | 10/1997 | Carling et al. |
| 5,682,874 A | 11/1997 | Grabenkort et al. |
| 5,730,158 A | 3/1998 | Collins et al. |
| 5,743,251 A * | 4/1998 | Howell et al. ......... 128/200.14 |
| 5,756,995 A | 5/1998 | Maswadeh et al. |
| 5,765,724 A | 6/1998 | Amberg et al. |
| 5,819,726 A * | 10/1998 | Rubsamen et al. .... 128/200.14 |
| 5,823,178 A | 10/1998 | Lloyd et al. |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,914,122 A | 6/1999 | Otterbeck et al. |
| 5,932,249 A | 8/1999 | Gruber et al. |
| 5,932,315 A | 8/1999 | Lum et al. |
| 5,944,025 A | 8/1999 | Cook et al. |
| 5,954,979 A | 9/1999 | Counts et al. |
| 5,957,124 A | 9/1999 | Lloyd et al. |
| 5,958,378 A * | 9/1999 | Waldrep et al. ................ 424/45 |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,071,554 A | 6/2000 | Isomura et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |

| | | |
|---|---|---|
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 2001/0032647 A1 | 10/2001 | Schuster et al. |

FOREIGN PATENT DOCUMENTS

| | | |
|---|---|---|
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |
| WO | 01/12319 A | 3/2001 |
| WO | 01/43800 A | 6/2001 |
| WO | 01/81182 A | 11/2001 |

OTHER PUBLICATIONS

Hou, Shuguang et al. *Solution Stability of Budensonide in Novel Aerosol Formulations* Abstract No. 2582, Solid State Physical Pharmacy, Nov. 17, 1998, p. S-307.

Kousaka, Yasuo et al., "Generation of Aerosol Particles by Boiling of Suspensions", Aerosol Science and Technology, 21:236-240 (1994).

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766-770, Jul. 1980.

Written Opinion dated Dec. 24, 2003 for PCT/US02/30871.

Notification of Transmittal of International Preliminary Examination Report dated Apr. 29, 2004 for PCT/US02/30871.

Benjamin, Y. H. Liu et al., "A Condensation Aerosol Generator for Producing Monodispersed Aerosols in the Size Range 0.036μ to 1.3μ", Journal De Recherches Atmospheriques, 1996, pp. 397-406.

* cited by examiner

METHOD AND APPARATUS FOR GENERATING AN AEROSOL

This application is a continuation of application Ser. No. 09/560,510, filed on Apr. 27, 2000 now abandoned.

The present invention relates generally to an apparatus and method for generating aerosols without compressed gas propellants.

BACKGROUND OF THE INVENTION

Aerosols are useful in a wide variety of applications. For example, it is often desirable to treat respiratory ailments with, or deliver medicaments by means of, aerosol sprays of finely divided particles of liquid and/or solid, such as powders, liquid medicaments, and the like, which are inhaled into a patient's lungs. Aerosols are also used for such purposes as providing desired scents to rooms, applying scents to the skin, and delivering paint and lubricant, for example.

Various techniques are known for generating aerosols, particularly in the field of medicine. For example, U.S. Pat. Nos. 4,811,731 and 4,627,432 both disclose devices for administrating medicaments to patients in which a capsule is pierced by a pin to release medicament in powder form. The user inhales released medicament through an opening in the device. Medicaments in liquid form are known to be delivered by generation of an aerosol with a manually operated pump. The pump draws liquid from a reservoir and forces it through a small nozzle opening to form a fine spray.

Both of these methods of generating an aerosol for the delivery of medicaments suffer from problems. The aerosols produced by these techniques contain substantial quantities of particles or droplets which are too large to be inhaled. Further, it is difficult to synchronize the inhalation of the medicament with the pumping of the aerosol device or the release of the powder. Persons who have difficulty in generating a sufficient flow of air through the device to properly inhale the medicaments, such as asthma or emphysema sufferers, have particular difficulty in using these devices.

An alternate means of delivering a medicament is generating an aerosol including liquid or powder particles by means of a compressed propellant, usually a chloro-fluoro-carbon (CFC) or methyl chloroform, which entrains the medicament, usually by the Venturi principle. Such inhalers are usually operated by depressing a button to release a short charge of the compressed propellant which contains the medicament through a spray nozzle, allowing the propellant encapsulated medicament to be inhaled by the user. However, it is again difficult to properly synchronize the inhalation of the medicament with depression of the actuator. Further, large quantities of medicament or other materials are not suitably delivered by this method. This method is better suited to delivery of such materials as antiperspirants, deodorants and paints, for example.

Most known aerosol generators also are unable to generate aerosols having an average mass median aerosol diameter (MMAD) less than 2 to 4 microns, and are incapable of delivering high flow rates, such as above 1 milligram per second, with particles in the range of 0.2 to 2.0 microns. A high flow rate and small particle size are particularly desirable for better penetration of the lungs during medicament administration, such as for asthma treatment.

Large particles generated by aerosol generators may be deposited in the mouth and pharynx of the patient, rather than inhaled into the lungs. Further, what is inhaled may not penetrate the lungs deeply enough. Therefore, it is known to add a spacer chamber to a pressurized inhaler mechanism in order to allow the propellant time to evaporate, decreasing the mass median aerosol diameter of the particles. See, for example, U.S. Pat. No. 5,855,202 to Andrade and *Eur. Respir. J.* 1997; 10:1345–1348. Particles from aerosol generators may have an MMAD of 5–6 µm. The use of a spacer chamber in such a case reduces the particle MMAD to about 1.5 µm or greater, enhancing medicament deposition in the lung as opposed to the mouth or throat. See, for example, *Eur. Respir. J.* 1997, 10:1345–1348; *International Journal of Pharmaceutics*, 1 (1978) 205–212 and *Am. Rev. Respir. Dis.* 1981, 124:317–320.

Spacer chambers also are known to affect the output of the aerosol device because of the static charge which may be created therein. Medicament particles may be deposited in spacer chambers by electrostatic attraction to the spacer chamber wall, by inertial impaction, or by gravitational settling over time. Further, different medicaments behave differently within such spacer chambers based on particle size, particle charge, and the like. Thus, loss of medicament occurs within spacer chambers and is a drawback to effective spacer chamber use. See *Eur. Respir. J.* 1997; 10: 1345–1348.

The aerosol generator (CAG) described in U.S. Pat. No. 5,743,251, herein incorporated by reference, and further described in *Respiratory Drug Delivery VI*, Eds. R. N. Dalby et al., Interpharm Press, IL (1998) pp 97–102, has many advantages over other aerosol generators. In general, the CAG operates by supplying a material in liquid form to a flow passage, such as a tube or capillary, and heating the flow passage so that the material volatilizes and expands out of the open end of the flow passage. The volatilized material combines with ambient air in such a manner that the volatilized material condenses to form an aerosol. The aerosol therefore contains no propellant, and has a mass median aerosol diameter of less than about 2 microns, generally between about 0.2 and about 2 microns, and preferably between about 0.2 and about 1 micron.

However, like other aerosol generators, some material can be lost during aerosol generation to the CAG device itself. It has been found that some aerosol particles can deposit on the end of the capillary or tube, thereby retaining the aerosol particles within the device itself. This phenomenon appears in part to be solute dependent. Further, if used to deliver medicament to the lungs of a patient, some aerosolized medicament can be lost to the throat and mouth of the patient. Because the CAG produces very fine particles, the particles may potentially be exhaled before settling fully into the patient's lungs, diminishing the amount of medicament delivered to the patient.

It is desirable to achieve a particle size of an aerosol which can penetrate deep into the lungs. It is further desirable to have the same or approximately the same mass median aerosol diameter for the aerosolized liquid and solid components. Further, it is desirable to minimize loss of the aerosol to the aerosol generator, as well as to the mouth and throat of the patient. One or more of these attributes can be achieved by the methods and apparatus described herein.

SUMMARY OF THE INVENTION

In accordance with one preferred embodiment of the present invention, the flow passage of the aerosol generator can be coated at the open end with an electrically conductive substance, such as a metal. In a second preferred embodiment, the flow passage can be made entirely of an electrically conductive material, such as stainless steel.

In accordance with another embodiment of the present invention, a spacer chamber can be added at the open end of the flow passage. Such a spacer chamber facilitates the enlargement of the mass median aerosol diameter of the aerosol particles generated.

In accordance with yet another embodiment of the present invention, an aerosol can be provided wherein the mass median aerosol diameter of the liquid and solid components of the aerosol are approximately equal, such as in the case where the aerosol is generated from a mixture of budesonide in triethylene glycol.

In accordance with yet another embodiment of the present invention, an aerosol can be provided wherein the MMAD of the liquid and solid components of the aerosol are different, such as in the case where the aerosol is generated from a mixture of budesonide in propylene glycol.

BRIEF DESCRIPTION OF THE DRAWINGS

The features and advantages of the present invention are well understood by reading the following detailed description in conjunction with the drawings in which like numerals indicate similar elements and in which:

FIG. 5 is a graph showing increase in particle size with use of a spacer chamber;

FIG. 6 is a graph showing increase in particle size over time with use of a spacer chamber;

DETAILED DESCRIPTION

An aerosol generator will be described in preferred embodiments wherein the usage is for medicament administration, particularly to the lungs of a person such as someone suffering from asthma, emphysema or other like disorders.

Figure 1:
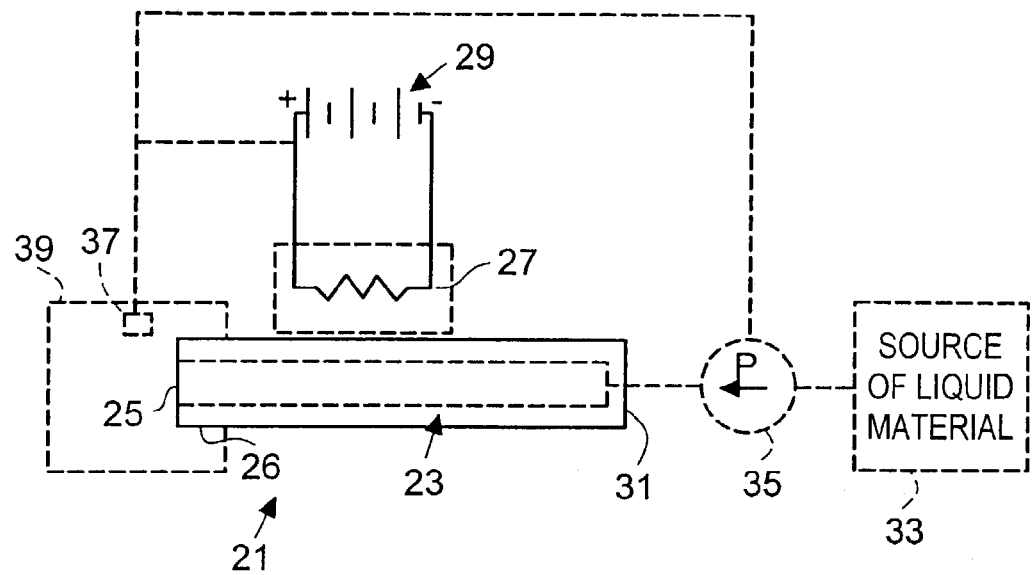
FIG. 1 is a schematic view of an aerosol generator according to a first embodiment of the present invention.

An aerosol generator 21 according to a first embodiment of the present invention is schematically shown with reference to FIG. 1. The aerosol generator 21 includes a flow passage 23 having an open end 25. A heater 27 is positioned adjacent to at least a portion of the flow passage 23, but preferably in a way that provides a heated zone around the flow passage that maximizes heat transfer throughout the heated zone. The heater 27 is connected to a power supply 29, preferably a D.C. power supply such as a battery.

In operation, a material (not shown) in liquid form is introduced to the flow passage 23. The heater 27 heats the portion of the flow passage 23 to a sufficient temperature to volatilize the liquid material. In the case of an organic liquid material, the heater preferably heats the liquid material just to the boiling point of the liquid material, and preferably maintains the surface temperature of the flow passage 23 below 400° C., as most organic materials are not stable when they are exposed to temperatures above that temperature for periods of time. The volatilized material expands out of the open end 25 of the flow passage 23. The volatilized material mixes with ambient air outside of the flow passage and condenses to form particles, thereby forming an aerosol.

In a presently preferred embodiment, the flow passage 23 is a capillary or tube, or a portion thereof. The flow passage 23 is preferably about 1.4 to 1.5 cm long and has an inside diameter of between 0.05 and 0.53 millimeter. A particularly preferred inside diameter of the flow passage is approximately 0.1 millimeter. The wall thickness is preferably about 0.0025 inch (0.064 mm). Those skilled in the art will recognize that flow passages of other parameters may be used dependent on many factors, such as the overall size of the aerosol generator desired, the material to be volatilized, the amount of material to be delivered, and the like. The flow passage 23 is preferably a portion of a fused silica capillary tube or an aluminum silicate ceramic capillary tube. However, other substantially non-reactive materials capable of withstanding repeated heating cycles and generated pressures and having suitable heat conduction properties may also be used.

The flow passage 23 preferably has an electrically conductive sleeve 26 surrounding it at the open end 25. The sleeve 26 is preferably stainless steel, though other electrically conductive materials may be used, for example, copper, aluminum and the like. It is preferred that the material of the sleeve 26 is capable of withstanding repeated heating cycles and generated pressures and has suitable heat conduction properties. It is preferable that the sleeve is also non-reactive with the vaporized liquid. The addition of an electrically conductive sleeve 26 diminishes medicament deposition at the open end 25 of the flow passage 23, and further has been found to improve the particle size distribution of the aerosol such that the deposition of medicament in the lungs is improved when the aerosol generator is used to deliver medicament. The sleeve 26 can be sized to accommodate the flow passage, e.g., a sleeve approximately 2 mm in length with a 24 gauge internal diameter and wall thickness of about 0.005 inch (0.13 mm) fitted over the capillary tube at the open end. One skilled in the art will recognize that the dimensions of the sleeve can be varied in accordance with those of the flow passage.

According to another embodiment, the entire flow passage 23 can be constructed of an electrically conductive material, such as stainless steel. Again, other electrically conductive materials can be used so long as they are non-reactive, and capable of withstanding repeated heating cycles and generated pressures and have suitable heat conduction properties. An electrically conductive flow passage 23 further reduces deposition at the open end 25 of the flow passage 23, thus reducing deposition within the aerosol generator and altering the aerosol particle size distribution in such a way as to minimize deposition within the mouth and throat of a patient using the aerosol generator for medicament administration. If desired or necessary, an inside wall of the flow passage 23 may be provided with a coating for reducing the tendency of material to stick to the wall of the flow passage, thereby minimizing clogging of the flow passage.

The deposition of material at the open end 25 of the flow passage 23 appears to be material specific. For example, medicaments with low volatility appear to coagulate more at the open end 25 of the flow passage 23, elsewhere within the aerosol generator and may coagulate in the mouth and throat of a patient to whom the medicament is administered. While not wishing to be bound by theory, it is believed that the medicament or other material may form an electrostatic charge during aerosol condensation. Use of an electrically conducting material around the open end 25 of the flow passage 23, or for the flow passage 23 itself, is believed to discharge the electrostatic charge, leaving neutral medicament particles. This allows for a more even distribution of the particles and prevents attraction of the particles to surfaces of the aerosol generator and to the patient's mouth and throat due to static electricity, thereby lowering overall loss of the aerosol before reaching the desired target site. However, the flow passage 23 preferably does not impart an electric charge to the particles, but rather removes an electric charge, making the particles neutral at the time they exit the open end 25 of the flow passage 23.

The flow passage 23 may be closed at a second end 31 and material in liquid form may be introduced into the flow passage 23 through the open end 25 when it is desired to form an aerosol. Thus, when the liquid material is heated by the heater 27, the volatilized material is only able to expand by exiting the flow passage 23 through the open end 25. However, it is preferred that the second end 31 of the flow passage be connected to a source 33 (shown by dotted lines in FIG. 1) of liquid material. The liquid material volatilized by the heater 27 in the portion of the flow passage 23 is prevented from expanding in the direction of the second end 31 of the flow passage, and is forced out of the open end 25 of the flow passage, as a result of back pressure of liquid from the source 33 of liquid material. The back pressure of the liquid is preferably between about 20 to 30 psi.

The heater 27 is preferably an electrical resistance heater. According to a preferred embodiment, the heater 27 is a heater wire having an outside diameter of 0.008 inches, a resistance of 13.1 ohms per foot, and a specific heat of 0.110 BTU/lb ° F. The composition of the heater wire is preferably 71.7% iron, 23% chromium, and 5.3% aluminum. Such a heater wire is available from Kanthal Furnace Products, Bethel, Conn. One skilled in the art will recognize other heater parameters and materials which may be used dependent upon the size of the aerosol generator, the material composition of the flow passage, the heat needed to volatilize the desired material in liquid form, and the like.

Figure 2A:
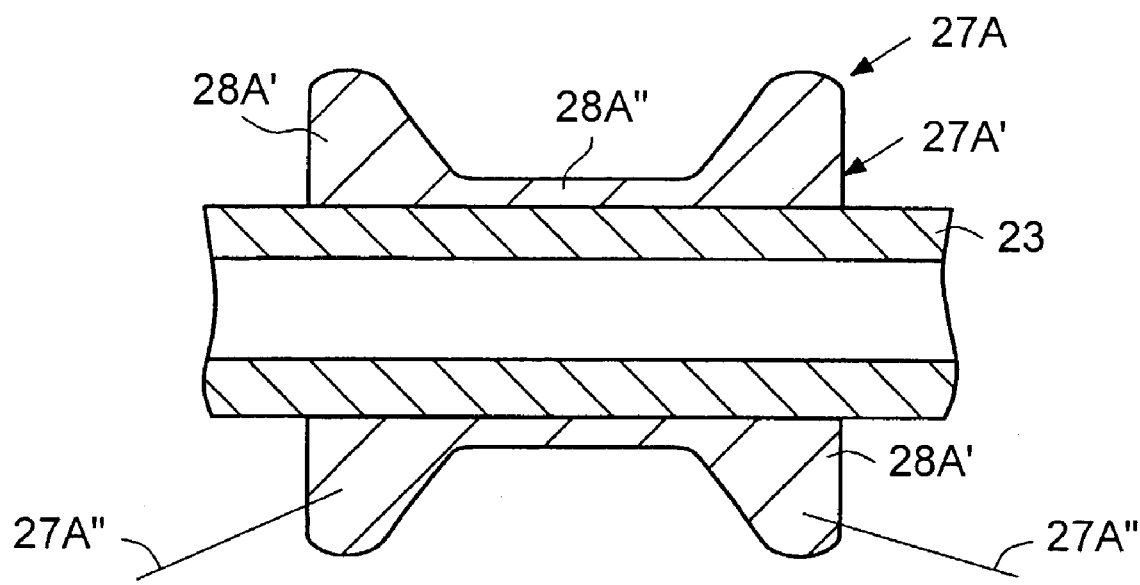
FIGS. 2A and 2B are schematic views of a portion of an aerosol generator including heaters according to embodiments of the present invention.
Figure 2B:
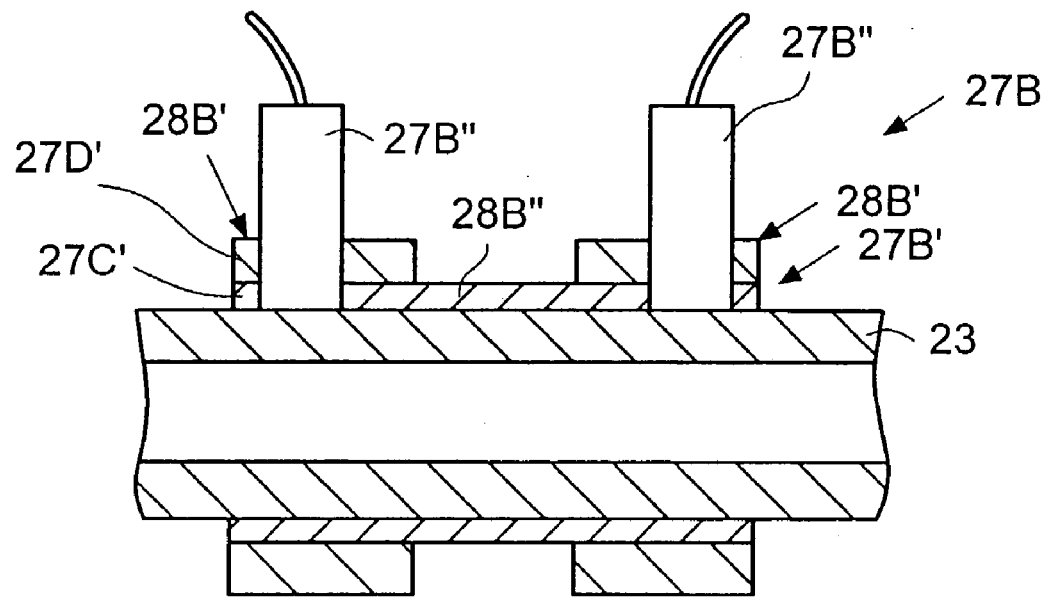

According to another preferred embodiment, the heater 27A and 27B shown in FIGS. 2A and 2B, respectively, includes a thin platinum layer 27A'. and 27B', respectively, which is deposited on the outside of a lapped ceramic capillary flow passage 23 serving as a substrate. In addition to the aluminum silicate ceramic capillary noted above, the flow passage may include a ceramic such as titania, zirconia, or yttria-stabilized zirconia which does not experience oxidation at normal operating temperatures after repeated cyclings. Preferably the ceramic of the flow passage is alumina having approximately a 99% purity, and more preferably approximately a 99.6% purity, such as is available from the Accumet Engineering Corporation of Hudson, Mass.

The flow passage and the heater layer preferably have a roughly matching coefficient of thermal expansion to minimize thermally induced delamination. The ceramic has a determined roughness to affect the electrical resistance and to achieve adhesion of the deposited platinum layer. The platinum layer does not experience oxidation degradation or other corrosion during projected life cycles.

The thin film heater layer is deposited on the flow passage 23. The heater layer is preferably a thin platinum film having a thickness of, e.g., less than approximately 2 µm, though other thicknesses may be used. The heater layer is deposited onto the capillary by any suitable method such as DC magnetron sputter deposition, e.g., using an HRC magnetron sputter deposition unit, in argon at $8.0 \times 10^{-3}$ Torr. Alternatively, other conventional techniques such as vacuum evaporation, chemical deposition, electroplating, and chemical vapor deposition are employed to apply the heater layer to the flow passage.

The surface morphology of the flow passage substrate, particularly of a ceramic capillary, is important to accomplish a successful deposition of the heater layer. Preferably, the flow passage 23 is lapped by a conventional serrated knife. Typical lapped alumina has an unpolished surface roughness between approximately 8 and 35 microinches. The ceramic flow passage substrate is then polished to a surface roughness having an arithmetic average greater than approximately one microinch and, more specifically, between one and approximately 100 microinches, and most preferably between 12 and 22 microinches. If the substrate is polished to further reduce surface roughness as in conventional ceramic substrate preparation, i.e., to a surface roughness of one microinch or less, an adequate deposition interface will not be formed.

As seen in FIG. 2A, the heater layer 27A' is coupled to the power supply by means of appropriate contacts 27A" for resistive heating of the heater layer. As seen in FIG. 2B, the heater layer 27B' is coupled to the power supply by conductive posts 27B" for resistive heating of the heater layer. The contacts or posts preferably have a lower resistance than the associated heater layer to prevent or reduce heating of these connections prior to heating of the heater layer. As seen in FIG. 2A, the contacts 27A" may comprise a gold coated tungsten wire, such as a W-wire wool (commercially available from the Teknit Corporation of New Jersey) which is gold coated. Alternatively, the contacts may comprise copper leads. The contacts 27A" contact the platinum heater layer 27A' on or in the heater layer top surface or at any other location so long as an adequate electrical contact is achieved. The contacts 27A' may be electrically connected to mounds 28A' of the platinum heater layer 27A', the heater layer further having an active area 28A" for heating the flow passage 23 therebetween. The resistance of the heater layer 27A' is affected by the morphology of the flow passage 23.

As seen in FIG. 2B, electrically conductive contact posts 27B" may be used instead of the above-described contact arrangements and may be formed to improve the mechanical strength of the assembly. The contact posts are connected to the outside of the flow passage 23 prior to deposition of the heater layer 27B' and are connected to the power supply by means of wires. The contact posts may be comprised of any desired material having good electrical conductance such as copper or copper alloys such as phosphur bronze or Si bronze, and are preferably copper or any alloy having at least approximately 80% copper. The posts 27B", or a bonding layer, as discussed below, provide a low electrical resistance connection for use with a desired current. If copper or a copper alloy is not employed for the posts, then preferably an intermediate copper bonding layer (not shown) is connected by any conventional technique to the end of the post to permit bonding between the post and the flow passage 23 without affecting the electrical path.

The connection of the ends of the posts 27B" to the flow passage 23 is preferably achieved by eutectic bonding wherein a surface of copper is oxidized, the resulting copper oxide surface is contacted with the ceramic flow passage substrate, the copper-copper oxide is heated to melt the copper oxide but not the copper such that the melted copper oxide flows into grain boundaries of the ceramic, and then the copper oxide is reduced back to copper to form a strong bond. This connection can be achieved by a eutectic bonding process such as used by Brush Wellman Corporation of Newbury Port, Mass.

Next, the platinum heater layer 27B' is applied to the ceramic flow passage 23. The heater layer comprises an initial layer 27C' extending around the flow passage 23 and the posts 27B" and a contact layer 27D' which electrically connects the posts to the initial layer. The active heating area 28B" is defined on the portion of the heater layer 27B' which is not covered by the contact layer 27D' as a result of masking the heating area prior to applying the contact layer. Mounds or thick regions 28B' are formed by the contact layer 27D' around the posts 27B" and rise from the flow passage surface to function as contacts. In the embodiments illustrated in FIGS. 2A and 2B, by providing mounds or graded regions of platinum in the heater layer such that it is thicker at the contacts or posts than at the active portion, a stepped resistance profile results which maximizes resistance in the active portion of the heater layer.

When the flow passage 23 (FIG. 1) is electrically conductive, it is connected to the power supply by two lengths of heating wire, preferably copper, which are bonded directly onto the capillary 23 (not shown) for resistive heating. A heating layer is not necessary in this case because the flow passage 23 itself acts to conduct heat.

The power supply 29 is sized to provide sufficient power for the heating element 27 that heats the portion of the flow passage 23. The power supply 29 is preferably replaceable- and rechargeable and may include devices such as a capacitor or, more preferably, a battery. For portable applications, the power supply is, in a presently preferred embodiment, a replaceable, rechargeable battery such as four nickel cadmium battery cells connected in series with a total, non-loaded voltage of approximately 4.8 to 5.6 volts. The characteristics required of the power supply 29 are, however, selected in view of the characteristics of other components of the aerosol generator 21, particularly the characteristics of the heater 27. One power supply that has been found to operate successfully in generating an aerosol from liquid propylene glycol is operated continuously at approximately 2.5 Volts and 0.8 Amps. The power supplied by the power supply operating at this level is close to the minimal power requirements for volatizing propylene glycol at a rate of 1.5 milligrams per second at atmospheric pressure, illustrating that the aerosol generator 23 may be operated quite efficiently.

The aerosol generator 23 may generate an aerosol intermittently, e.g., on demand, or, as discussed further below, continuously. When it is desired to generate an intermittent aerosol, the material in liquid form may be supplied to the portion of the flow passage 23 proximate the heater 27 each time that it is desired to generate the aerosol. Preferably, the material in liquid form flows from the source 33 of material to the portion of the flow passage 23 proximate the heater 27, such as by being pumped by a pump 35 (shown by dotted lines).

If desired, valves (not shown) may be provided in line between the portion of the flow passage 23 proximate the heater 27 and the source 33 of the material to interrupt flow. Preferably, the material in liquid form is pumped by the pump 35 in metered amounts sufficient to fill the portion of the flow passage 23 proximate the heater 27 so that substantially only the material in that portion of the flow passage will be volatilized to form the aerosol. The remaining material in the line between the source 33 of material and the portion of the flow passage 23 prevents expansion of the volatilized material in the direction of the second end 31 of the flow passage.

When it is desired to generate an aerosol intermittently for medicament inhalation, the aerosol generator 23 is preferably provided with a breath-actuated sensor 37 (shown by dotted lines), which preferably forms part of a mouthpiece 39 (shown by dotted lines) disposed proximate the open end 25 of the flow passage 23, for actuating the pump 35 and the heater 27 so that material in liquid form is supplied to the flow passage 23 and the material is volatilized by the heater. The puff-actuated sensor 37 is preferably of the type that is sensitive to pressure drops occurring in the mouthpiece 39 when a user draws on the mouthpiece. The aerosol generator 23 is preferably provided with circuitry such that, when a user draws on the mouthpiece 39, the power supply activates the pump 35 to supply material in liquid form to the flow passage 23 and the power supply activates the heater 27.

A breath-actuated sensor 37 suitable for use in the aerosol generator may be in the form of a Model 163PC01D35 silicon sensor, manufactured by the MicroSwitch division of Honeywell, Inc., Freeport, Ill., or an SLP004D 0–4" $H_2O$ Basic Sensor Element, manufactured by SenSym, Inc., Milpitas, Calif., for example. Other known flow-sensing devices, such as those using hot-wire anemometry principles, are also believed to be suitable for use with the aerosol generator.

The mouthpiece 39 is disposed proximate the open end 25 of the flow passage 23 and facilitates complete mixing of the volatilized material with cooler ambient air such that the volatilized material condenses to form particles. For medicament delivery applications, the mouthpiece 39 is preferably designed to permit passage of approximately 60–100 liters of air per minute without substantial resistance, such a flow rate being the normal flow for inhalation from an inhaler. Of course, the mouthpiece 39, if provided, may be designed to pass more or less air, depending upon the intended application of the aerosol generator and other factors, such as consumer preferences. A preferred mouthpiece for a hand held asthma inhaler is approximately 1 inch in diameter and between 1.5 and 2 inches in length, with the open end 25 of the flow passage 23 centered at an end of the mouthpiece.

Figure 1A:
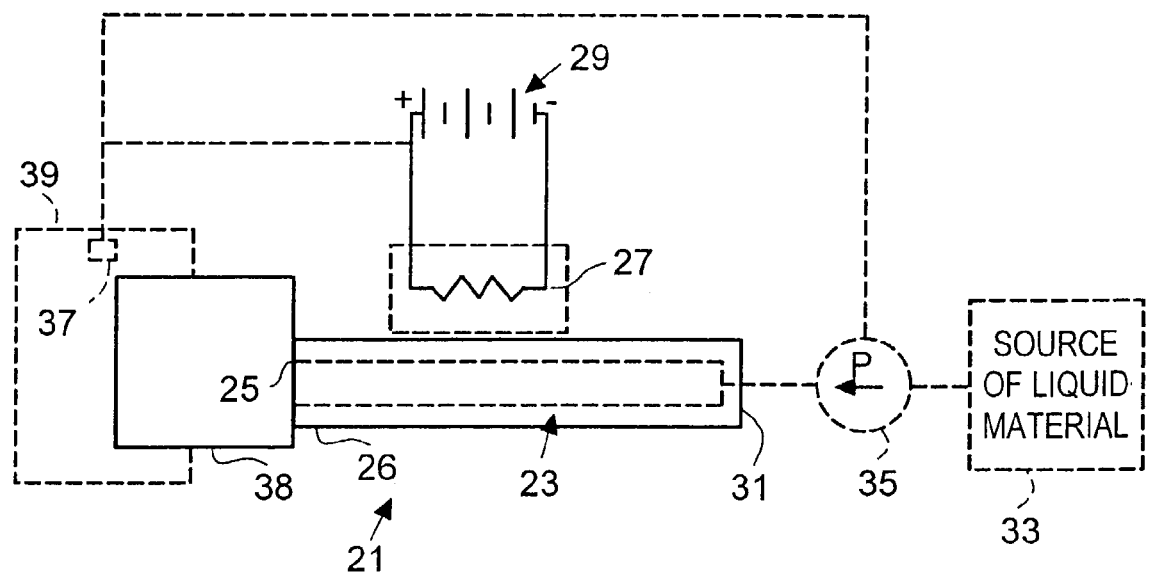
FIG. 1A is a schematic view of an aerosol generator according to a second embodiment of the present invention.

Depending on the desired aerosol droplet size, a spacer chamber 38 may be added at the open end 25 of the flow passage 23 before the mouthpiece 39 (see FIG. 1A). The spacer chamber 38 functions in a manner opposite to known spacer chambers used in aerosol generators, which reduce particle size by allowing evaporation of the propellent entraining the material to be delivered. The aerosol generator described herein produces extremely small (e.g., submicron sized) particles and the spacer chamber functions to increase the average MMAD of the particles. Larger particles may be desired for various applications, such as medicament delivery wherein the use of larger particles would decrease the risk of exhalation of the particles before settling within the lungs of a patient, for example.

The use of a spacer chamber 38 with the aerosol generator described herein unexpectedly can increase the particle size from an average size of $\leq 0.50$ μm to greater than 0.50 μm, preferably to at least about 1.0 μm or greater, and more preferably to about 1.0–5.0 μm. While not wishing to be bound by theory, it is believed the particles collide with one another in the spacer chamber over time, allowing growth of the aerosol particles through coagulation, aggregation and/or coalescence of the particles. The resultant particle size is determined by the size and shape of the spacer chamber 38, as well as the amount of time during which the particles are located therein. These factors may also affect the amount of particles deposited within the spacer chamber 38.

An increase in the length of time in which the particles are within the spacer chamber 38, or a decrease in the internal volume of the spacer chamber 38, both result in larger particle sizes of the emitted aerosol. The particles generally have a narrow MMAD distribution. However, the MMAD distribution can be increased by holding the particles in the spacer chamber 38 for a longer period of time, or by increasing the size of the spacer chamber 38. Thus, dependent upon the length of time for which the particles are held in the spacer chamber 38, or the size of the spacer chamber 38, a more homogeneous or a more heterogeneous mixture of particle sizes within a desired range can be obtained. Each spacer has a critical holding time beyond which the particle size distribution does not significantly change, or ceases to change, and therefore the aerosol particle size is stable. See Example 6 and FIG. 9.

The optimum spacer chamber size and shape can be selected based on the material to be delivered, the desired particle size, and the configuration of the aerosol generator itself, including the material used for the flow passage, the characteristics of the power supply and heater, and/or other like factors. It should be noted that the smaller the spacer chamber size, and therefore the larger the particles generated, the more likely the particles are to deposit within the spacer chamber itself. Therefore, as larger particles are generated, more particles are lost to the spacer chamber and therefore are not available for delivery to the desired target site.

Figure 3:
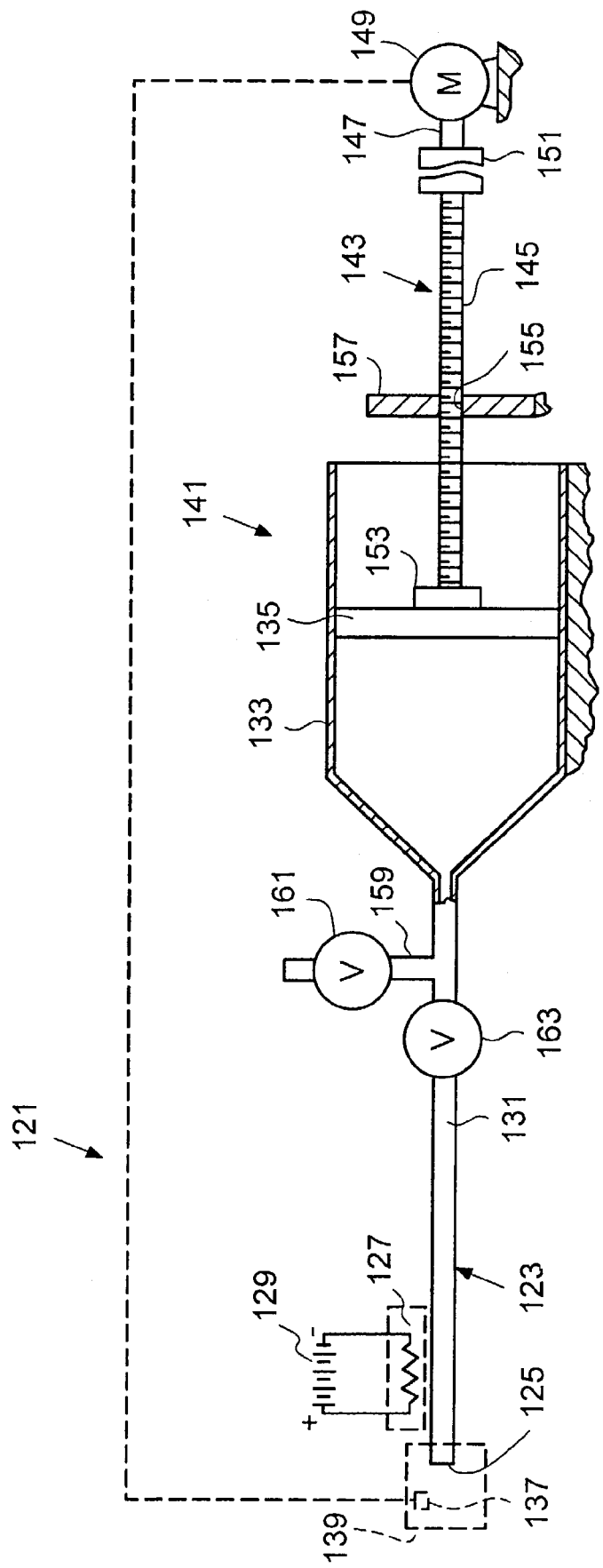
FIG. 3 is a schematic view of an aerosol generator according to a third embodiment of the present invention.

An aerosol generator 121 according to another embodiment of the present invention is seen with reference to FIG. 3. The basic components of the aerosol generator 121 are substantially the same as the components of the aerosol generator 21 shown in FIG. 1, the aerosol generator 121 shown in FIG. 3 including a presently preferred liquid material supply assembly 141. The aerosol generator 121 includes a flow passage 123 having an open end 125, a heater 127 attached to a portion of the flow passage 123 proximate the open end, and a power supply 129 for supplying power to the heater.

A second end 131 of the flow passage 123 extends to a reservoir or source 133 of liquid material, such as a cylinder of a syringe, and the liquid material is delivered to the flow passage through the second end 131 thereof by means of a pump 135, such as a piston of the syringe. A mouthpiece 139 and breath-actuated sensor 137 (both shown by dotted lines) may be provided as well, in substantially the same manner as discussed above with regard to the aerosol generator 23.

As with aerosol generator 23, it is preferred that the flow passage 123 have an electrically conductive sleeve at the open end 125, or, more preferably, that the flow passage 123 itself be electrically conductive. Further, a spacer chamber may be provided between the open end 125 of the flow passage and mouthpiece 139, as described with regard to aerosol generator 23.

The illustrated syringe pump 141, including the cylinder 133 and piston 135, facilitates delivery of liquid material to the flow passage 123 at a desired flow rate. The syringe pump 141 is preferably provided with an assembly 143 for automatically moving the piston 135 relative to the cylinder 133. The assembly 143 preferably permits incremental or continuous advancement or withdrawal of the piston 135 from the cylinder 133, as desired. If desired, of course, the piston 135 may alternatively be manually compressible.

The assembly 143 preferably includes a rod 145, at least a portion of which is externally threaded. Preferably, the rod 145 is attached at one end to a shaft 147 of a reversible motor 149, preferably an electric motor, such that operation of the motor causes the rod to rotate clockwise or counterclockwise, as desired. The rod 145 is preferably attached to the shaft 147 by means of a coupling 151 that permits axial movement of the rod relative to the shaft, but not rotational movement of the rod relative to the shaft.

An end of the rod 145 is attached to the piston 135. The rod 145 is preferably attached to the piston 135 by means of a bearing assembly 153 such that rotation of the rod does not cause rotation of the piston. However, if desired, the rod may be rigidly attached to the piston. The externally threaded portion of the rod 145 extends through an internally threaded opening 155 in a member 157, which may simply be a nut, which is fixed in position relative to the motor 149 and the cylinder 133, both of which are preferably also fixed in position.

Preferably, when the motor 149 is operated, the shaft 147 turns the rod 145 and the rod turns in the opening 155 relative to the fixed member 157. As the rod 145 turns in the opening 155, the end of the rod attached to the piston 135 is advanced or withdrawn from the cylinder 133, depending upon the thread of the rod and the opening and the direction in which the rod is turned. The coupling 151 permits the rod 145 to move axially relative to the shaft 147. Sensors (not shown) are preferably provided to ensure that the rod 145 is not moved excessively into or out of the cylinder 133. It will be appreciated that a liquid supply arrangement such as the above-described syringe pump 141 is well suited to supply liquid at a rate of 1 milligram/second or greater, as needed, and that, provided a sufficiently powerful heater 127 is provided, an aerosol may be continuously produced at a rate of 1 milligram/second or greater, which is understood to be a much greater rate of delivery of particles in sizes between 0.2 and 2 microns mass median aerosol diameter than is available with conventional aerosol medicament delivery systems.

It will often be desirable to minimize contact of the liquid in the cylinder 133 with oxygen, such as to avoid contamination or decomposition. To this end, the aerosol generator 121 is preferably provided with an arrangement for conveniently refilling the cylinder 133 of the syringe pump 141, such as a line or tube 159 having a valve 161 that may be opened as the piston 135 is withdrawn in the cylinder to draw liquid from another source of supply. Another valve 163 may be provided in the flow passage 123 to ensure that liquid flowing into the aerosol generator is charged into the cylinder and not inadvertently wasted by flowing out of the open end 125 of the flow passage. If desired, a three-way valve may be provided to alternatively permit flow from the cylinder 133 to the flow passage 123 and from the line 159 to the cylinder.

In addition, or in the alternative, the cylinder 133 and piston 135 may be configured to be easily replaced when emptied, such as by providing appropriate fittings where the end of the cylinder meets the second end 131 of the flow passage 123 and where the rod 145 is attached to the piston. A new, preferably hermetically sealed, piston 135 and cylinder 133 can be provided to replace a used piston and cylinder. Such an arrangement may be particularly desirable in applications such as hand held inhalers and the like.

The aerosol generator 121 may continuously generate an aerosol, such as by continuously operating the motor 149 and the heater 127 such that liquid material is continuously supplied to the flow passage 123 and the supplied liquid material is continuously volatilized. In addition, or in the alternative, the aerosol generator may intermittently generate an aerosol, such as by intermittently operating the motor 149 and the heater 127 such that a desired amount of liquid material is supplied to the flow passage 123 over a period of time and the heater is operated for a sufficient length of time to volatilize the supplied liquid, the motor and the heater thereafter being turned off. Intermittent operation in medicament delivery applications is preferably achieved by actuation of the motor 149 and the heater 127 by the breath-actuated sensor 137 in combination with appropriate interconnecting circuitry. Alternative actuating devices, e.g., push buttons, may, of course, be used.

Figure 4:
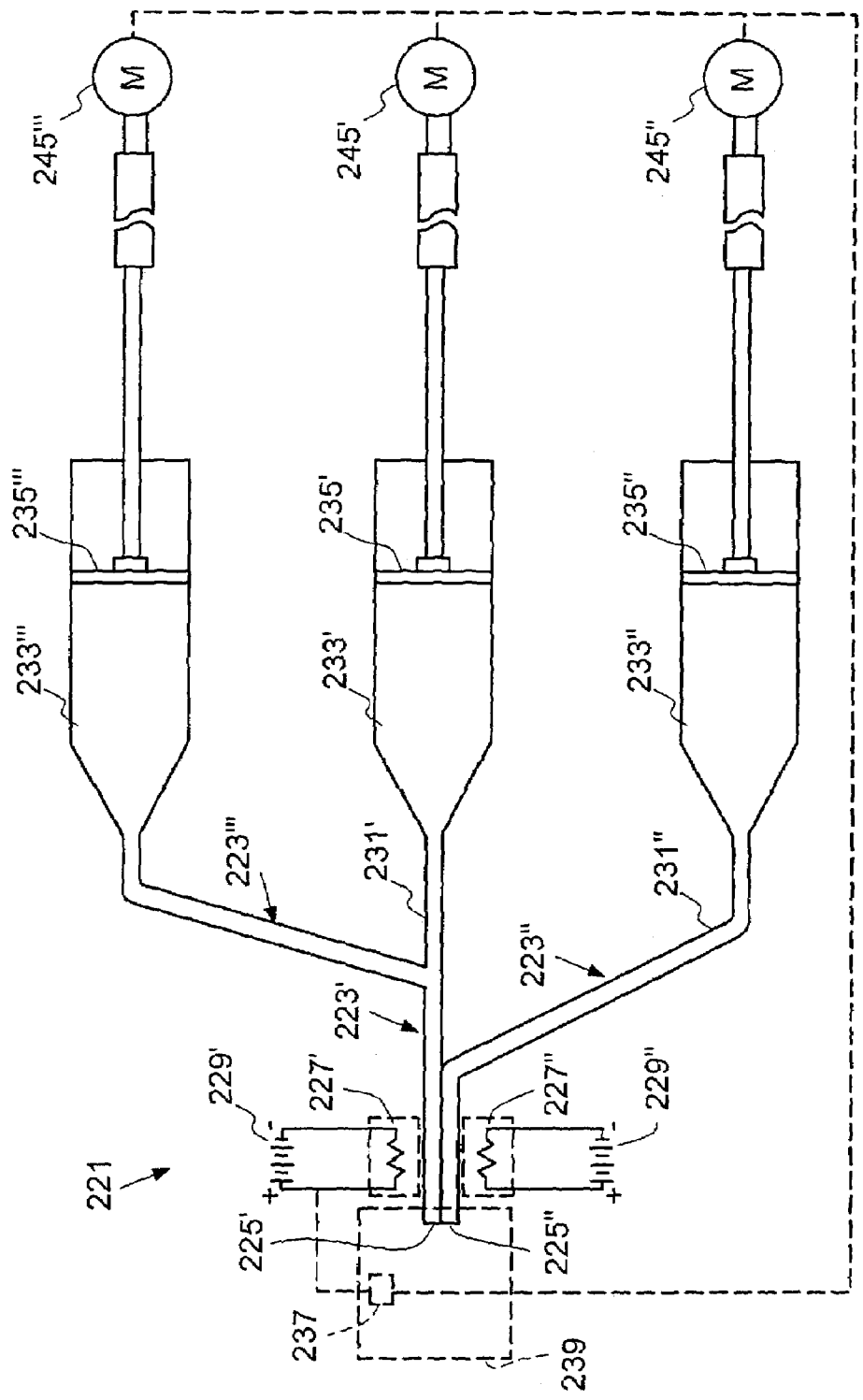
FIG. 4 is a schematic view of an aerosol generator according to a fourth embodiment of the present invention.

An aerosol generator 221 according to another embodiment of the present invention is seen with reference to FIG. 4. The aerosol generator 221 includes two or more separate aerosol generators, which may be substantially the same as the aerosol generator described above, in combination. The parallel aerosol generator arrangement facilitates forming a combination aerosol formed by mixing together two or more separately generated aerosols. The parallel aerosol generator arrangement is particularly useful where it is desired to form an aerosol comprising two or more materials which do not mix well in liquid form.

Each aerosol generator preferably includes a flow passage 223' and 223", respectively, each flow passage having an open end 225' and 225", respectively. Heaters 227' and 227" are preferably provided for each flow passage 223' and 223", respectively, although, in some applications, it may be convenient or possible to provide a single heater for heating both flow passages. The heaters are powered by power supplies 229' and 229", respectively. If desired, a single power supply may be used to power both heaters.

Each flow passage 223' and 223" is connected at its second end 231' and 231", respectively, to sources 233' and 233", respectively, of first and second liquid materials. The first and second liquid materials are advanced into the flow passages 223' and 223" by pumps 235' and 235", respectively. The pumps 235' and 235" may pump the first and second liquids at the same or different flow rates, as desired or necessary, and may be driven by separate driving means or by a common driving means, such as by the above-described automatic moving assembly. When the first and second liquid materials in the flow passages 223' and 223" are volatilized by the heaters 227' and 227", respectively, and expand out of the open ends 225' and 225" of the flow passages, respectively, the volatilized first and second materials are mixed together in a mixing chamber, such as a mouthpiece 239 or a spacer chamber (not shown), and mix with ambient air so that they condense and form an aerosol. A breath-actuated sensor 237 may be used to actuate components such as the one or more power supplies and one or more motors for driving the pumps.

Where liquids are conveniently miscible, it may also be desirable to combine, e.g., two or more liquids in one or more flow passages or a manifold in a location between a source 233' and 233''' of the liquids and a portion of the flow passage that is heated by the heater. The liquids may be supplied together to the flow passage 223' from the sources 233' and 233''' by separate pumps 235' and 235''', respectively, at the same or different flow rates, as desired or necessary, and the pumps may be driven by separate or common driving means. The heater 227' heats the flow passage 223' to a temperature sufficient to volatilize the mixed liquid materials, the volatilized mixed liquid materials expanding out of the open end 225' of the flow passage and condensing to form a combination aerosol. If desired, the combination aerosol formed of the pre-mixed liquids may be combined with other aerosols to form still further combination aerosols.

The characteristics of the aerosol generated by the aerosol generator according to the present invention are generally functions of various parameters of the aerosol generator and the liquid material supplied to the aerosol generator. For aerosols intended for inhalation, for example, it is desirable for the aerosol to be at approximately body temperature when inhaled and for the mass median aerosol diameter of particles of the aerosol to be less than 2 microns, preferably between 0.2 and 2 microns, and more preferably between 0.2 and 1 micron.

It has been observed that liquid materials such as propylene glycol and glycerol can be formed into aerosols having mass median aerosol diameters and temperatures in the preferred ranges. While not wishing to be bound by theory, it is believed that the extremely small mass median aerosol diameters of the aerosol according to the present invention are achieved at least in part as a result of the rapid cooling and condensation of the volatilized material that exits the heated flow passage. Manipulation of parameters of the aerosol generator such as the internal diameter of the flow passage, heat transfer characteristics of the flow passage, heating capacity of the heater, and the rate at which material in liquid form is supplied to the flow passage may affect aerosol temperature and mass median aerosol diameter.

Certain components in solid, i.e., powdered, form may be mixed with a desired liquid component so that the resulting solution is formed into an aerosol in the manner described above. Where the solid component is of the type that remains suspended in the particular liquid component used, the solid component is forced out of the open end of the flow passage with the volatilized liquid component. The resulting aerosol consists of particles resulting from the condensation of the volatilized liquid and solid component particles. When volatilized solid component particles are larger or smaller than the particles resulting from the condensation of the volatilized liquid component, the resulting aerosol may separate into its solid and liquid component over time, allowing separate deposition of the liquid and solid aerosolized components.

It is theorized that improved delivery of the aerosol will result from the solid component particles and liquid component particles having approximately the same MMAD once volatilized. To achieve the same volatilized particle size of the solid component and liquid component particles, covolatilization and cocoalecense of the solid and liquid are preferred.

While not wishing to be bound by theory, it is believed that the separation or covolatilization of the solid component and liquid component are an effect of the temperature and pump rate of the aerosol generator as well as of the physical characteristics such as melting point and boiling point of the solid component and liquid component and the mutual solubility profile of these ingredients as a function of the temperature to which they are heated. Assuming that a constant flow rate and temperature of the aerosol generator are desired, a like particle size between the aerosolized solid component and liquid component can best be achieved by altering either the solid component or liquid component used.

In the following examples, observations and test results using benzil and budesonide as solid components in the liquid components (which may be solvents or vehicles) of propylene glycol and triethylene glycol are discussed. The trends observed for these solid components and liquid components are expected to hold true for other combinations of materials.

Budesonide has a higher melting point than benzil. When used with propylene glycol as a solvent, aerosolized budesonide and propylene glycol have a different MMAD, while aerosolized benzil and propylene glycol have approximately the same MMAD. When triethylene glycol is the solvent, aerosolized benzil and triethylene glycol have approximately the same MMAD, and aerosolized budesonide and triethylene glycol have approximately the same MMAD. Thus, while not wishing to be bound by theory, it is believed that a solid which has a higher melting point, and therefore lower volatility, such as budesonide, requires a solvent having a higher molecular weight, such as triethylene glycol, in order to achieve covolatilization and cocoalescence of the solid component and solvent or vehicle.

A method for generating an aerosol according to the present invention will now be described with reference to the aerosol generator 221 shown in FIG. 4. A material in liquid form is supplied to the flow passage 223' having the open end 225'. The material supplied to the flow passage 223' is heated by the heater 227' to a temperature sufficient to volatilize the supplied material such that the volatilized material expands out of the open end 225' of the flow passage. The volatilized material condenses upon mixing with ambient atmospheric air, preferably in a mouthpiece 239, to form the aerosol.

Material may be intermittently supplied to the flow passage 223' and the supplied material may be intermittently heated to a temperature sufficient to volatilize the material by intermittently operating the heater 227' and the pump 235'. The breath-actuated sensor 237 may be used to intermittently actuate the heater 227' and the motor 245' for driving the pump 235' when a user draws on the mouthpiece 239. The pump 235' and the heater 227' may, however, be manually actuated, e.g., by a push button arrangement and appropriate circuitry. It will further be appreciated that the pump 235' and the heater 227' may be automatically actuated. For example, the pump 235' and the heater 227' may be actuated by a timer for periodic introduction of a medicament in aerosol form to a patient on a respirator. The pump 235' and the heater 227' may, further, be continuously operated to continuously form an aerosol.

If desired, a second material in liquid form may be supplied from a source of the second material 233" to a second flow passage 223" having an open end 225". The second material supplied to the second flow passage 223" is heated by a separate heater 227" to a temperature sufficient to volatilize the supplied second material such that the volatilized second material expands out of the open end 225" of the second flow passage. If desired, the second material supplied to the second flow passage 223" may be heated by the same heater 227' that heats the first flow passage 223'. The volatilized first material and the volatilized second material that expand out of the open ends of the flow passage 223' and the second flow passage 223", respectively, are mixed together with ambient air such that the volatilized material and the volatilized second material form first and second aerosols, respectively. The first and second aerosols are mixed with each other to form a combination aerosol including the first and second aerosols. The mixing of the first and second volatilized materials with each other and with air to form the first and second aerosols and the combination aerosol preferably takes place in a mixing chamber which, in the case of aerosol generators for medicament delivery, is preferably the mouthpiece 239 or a spacer chamber.

In addition to, or as an alternative to, mixing the first and second aerosols as described above, if desired, a third material in liquid form may be supplied from a third source 233''' of liquid material to, e.g., the flow passage 223', together with the first material. The first material and the third material supplied to the flow passage 223' are heated by the heater 227' to a temperature sufficient to volatilize the first material and the third material such that the volatized first material and third material expand out of the open end 225' of the flow passage together.

Solid particles may be suspended in solution in the liquid component supplied from the source of material. When the liquid component including the suspended solid particles is heated by a heater, the solid particles are forced out of the open end of the flow passage as the volatilized liquid component expands such that the aerosol includes condensed particles of the liquid component and the solid particles. The solid component, when suspended in solution, may be of a larger or smaller average diameter than particles of the liquid component in aerosol form, or may be approximately the same size. Moreover, the solid particles, when they form a part of the aerosol, may be of a larger or smaller average diameter than particles of the liquid component in aerosol form or may be approximately the same size.

It will be appreciated that embodiments of the aerosol generator according to the present invention may be fairly large, such as a table-top mounted item, but may also be miniaturized to be hand held. The ability of the aerosol generator to be miniaturized is, in large part, due to the highly efficient heat transfer between the heater and the flow passage which facilitates battery operation of the aerosol generator with low power requirements.

EXAMPLES

The Examples were conducted with the apparatus and in the methods described below unless otherwise indicated.

For purposes of performing experiments in connection with the aerosol generator described herein, a laboratory unit was designed which contained the basic elements of the generator, but which was modular in construction so that the various components could be exchanged after running. During most of the runs it was possible to measure the surface temperature of the heater and the power applied. Mass median aerosol diameter was obtained using a cascade impactor in accordance with the methods specified in the "Recommendations of the USP Advisory Panel on Aerosols on the General Chapters on Aerosols (601) and Uniformity of Dosage Units (905)," *Pharmacopeial Forum*. Vol. 20, No.

3, pp. 7477 et. seq. (May–June 1994), and aerosol mass was measured gravimetrically or chemically by HPLC as collected from the impactor.

In the Examples that follow, the aerosol generator included a flow passage of a section of fused silica capillary tubing, more particularly, a phenyl-methyl deactivated capillary guard column for gas chromatography, available from Restek Corporation, Bellefonte, Pa., which was carefully wrapped with a 0.008" OD, 13.1 ohms per foot, heating wire, marked K-AF, available from Kanthal Corp., Bethel, Conn., to form a 1.0 to 1.5 cm long heating zone. The wire was wrapped in a fashion that produced close, tight coils to insure good heat transfer to the flow passage. The point of the needle of a Model 750N 500 microliter syringe, available from Hamilton Company, Reno, Nev., was cut off and smoothed to yield a blunt end. The blunt end was connected to the flow passage using common gas chromatography capillary column hardware. Either a ceramic or quartz capillary (¼" inner diameter), slotted for electrical connections, was placed around the heated zone for insulation.

Alternatively, the aerosol generator included a stainless steel sleeve on the flow passage of a fused silica capillary tubing. The sleeve was a stainless steel sleeve of 2 mm length, 24 gauge (0.014 inch) internal diameter, 0.024 inch outer diameter and 0.005 inch wall thickness, such as that supplied by Small Parts Inc, Miami Lakes, Fla. (Cat # HTX-24TW-24, Hypo Tube 304 S/S 24 Ga—thin wall), placed around the fused silica capillary flow passage. The flow passage alternately comprised a stainless steel tube which was 1.4–1.5 cm long, 32 gauge (0.004 inch) internal diameter and 0.009 inch outer diameter with a 0.0025 inch wall thickness, such as that supplied by Small Parts Inc, Miami Lakes, Fla. (Cat # HTX-32TW-24, Hypo Tube 304 S/S 32 Ga—standard wall). When the flow passage was stainless steel, no separate heating layer was necessary as the current used to generate heat may be supplied directly through the metallic flow passage which may be directly or indirectly attached to a power source.

The syringe body was loaded onto a Model 44 programmable syringe pump, available from Harvard Apparatus, Inc., South Natick, Mass. The end of the flow passage was centered and supported inside a mouthpiece that was machined for mating to the induction port that connected to a MOUDI model 100 cascade impactor, available from MSP Corporation, Minneapolis, Minn., as per the "Recommendations of the USP Advisory Panel on Aerosols on the General Chapters on Aerosols (601) and Uniformity of Dosage Units (905)," Pharmacopeial Forum. Vol. 20, No. 3, pp. 7477 et. seq. (May–June 1994).

Electrical connections were made to the heater wire leads from a model TP3433A triple output DC power source, manufactured by Power Designs, Inc., Westbury, N.Y., and a microminiature open junction thermocouple was gently placed against one turn of the heater coil about midway along the heated zone. Computer controlled solid state switches were used to precisely time the start of the syringe pump with the power to the heater wire. Power and temperature measurements were recorded every tenth of a second by a computer using LAB TECH NOTEBOOK software, available from Laboratory Technologies, Wilmington, Mass., and a DT2801 I/O board, available from Data Translation, Inc., Marlboro, Mass.

The cascade impactor was operated according to the manufacturer's specifications. All runs were conducted with an impactor air flow rate of 30 liters per minute and a total aerosol production of less than 100 mg. A loading of 30 to 60 mg in the impactor gave fairly consistent results.

During the following runs, it was desired to apply sufficient power to the heater to heat the fluid in the flow passage so that it reached its boiling point and vaporized before it exited the flow passage. It was further desired to heat the vapor sufficiently to prevent condensation at the exit of the flow passage. There were losses to the surrounding environment which should be considered in the power equation, and these losses were and are device and device-design dependent.

In practice, with the particular aerosol generating device used during the following runs, the device was operated several times to determine the power required to hold the heater at a specific temperature in order to determine the losses to the surroundings. To obtain a rough estimate of total power required, the theoretical amount of energy required for heating and vaporization was added to the loss power. Several trial runs were performed to visually observe the vapor exiting the flow passage and the aerosol formation. When no condensation at the open end of the flow passage was seen, then the power was adjusted down until condensation occurred, after which enough additional power was added so that the device was operated just above the condensation threshold. It is contemplated that numerous refinements will be made to commercial aerosol generating devices and to the manner in which power levels are set and controlled in such devices.

The following examples reflect various runs performed with an aerosol generator set up and operated as described herein, unless otherwise indicated.

Certain abbreviations or terms used within the Examples are set forth below. Other abbreviations used, unless otherwise indicated, have the meaning set forth elsewhere herein, or the ordinary meaning in the art.

| | |
|---|---|
| ACI = | Andersen cascade impactor |
| CAG = | capillary aerosol generator |
| BUD = | budesonide |
| capillary holder = | aerosol generator apparatus |
| HPLC = | High Performance Liquid Chromatography |
| impactor or cascade impactor = | device for measuring the size of emitted particles (simulates lung deposition) |
| MMAD = | mass median aerosol diameter |
| n = | number of experimental runs made |
| PG = | propylene glycol |
| SD = | standard deviation |
| sec. = | seconds |
| TEG = | triethylene glycol |
| throat = | simulated passageway for emitted aerosol particles which connects the aerosol generation device with the impactor |
| USP = | United States Pharmacopeia |

Figure 14A:
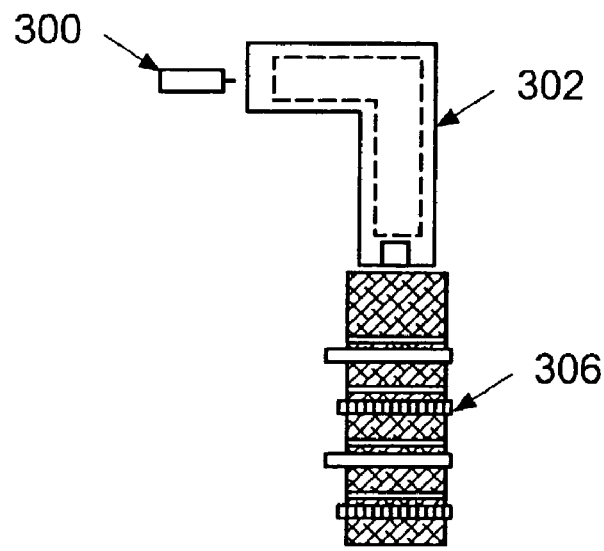
FIGS. 14A and B are a depiction of the general experimental apparatus used to test aerosols and determine their particle size.
Figure 14B:
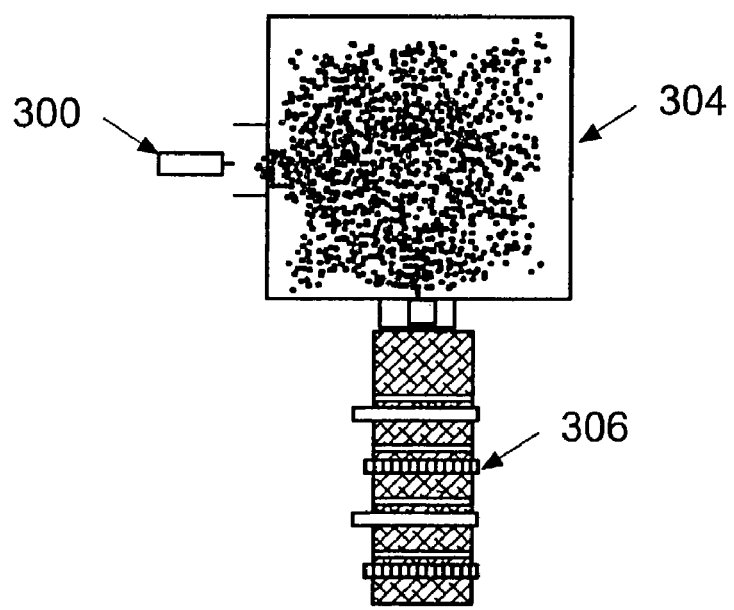

The schematic diagram of FIG. 14 depicts the general experimental set-up for sampling aerosols using an aerosol generator 300 emitting an aerosol into (a) a USP throat 302 or (b) a large volume spacer chamber box 304 atop a cascade impactor 306. Experiments and results are set forth below.

Flow Passage Tests

1. Stainless Steel vs. Glass Flow Passage with Glass Spacer Chamber

Budesonide spacer chamber deposition and aerosol particle size distribution of aerosols generated using a glass and stainless steel flow passage, respectively, were compared. The test solutions used for these experiments was 0.8% w/w budesonide in propylene glycol. Aerosols were generated and collected in a 500 ml glass spacer chamber for a period of 20 seconds. The glass spacer chamber was then connected to an Andersen cascade impactor (ACI) and the aerosol was sampled at a volumetric flow rate of 28.3 L/min. Washings were then collected from budesonide deposition sites and the mean (SD) particle size distribution of the aerosol was determined. As shown below, the budesonide particle size distribution for aerosols generated using the standard glass flow passage and the stainless steel flow passage were similar. In contrast, the observed deposition of budesonide in the glass spacer chamber was significantly reduced following aerosol generation using the stainless steel flow passage. This represents a significant improvement to the aerosol generator because it increases the amount of budesonide that is potentially respirable.

| Flow Passage | BUD deposition in spacer chamber | BUD MMAD |
| --- | --- | --- |
| Glass capillary (n = 5) | 43.5 (10.7) µg | 1.4 (0.1) µm |
| Stainless steel capillary (n = 7) | 5.07 (2.3) µg | 1.2 (0.2) µm |

2. Stainless Steel vs. Glass Flow Passage with Stainless Steel Spacer Chamber (USP Throat)

Budesonide in propylene glycol aerosol (0.8% w/w) was sampled directly into an Andersen cascade impactor via a USP stainless steel throat following generation using a stainless steel or glass flow passage, respectively. Aerosols were generated for a period of 20 seconds and sampled directly into the impactor via the throat entrance port at a volumetric flow rate of 28.3 L/min. Washings were then collected from budesonide deposition sites and the mean (SD) particle size distribution of the aerosol was determined. Similar-budesonide particle size distributions for aerosols generated using the standard glass flow passage and the stainless steel flow passage were observed, as shown below. The observed deposition of budesonide in the stainless steel throat was significantly reduced following aerosol generation using the stainless steel flow passage as compared to the glass flow passage. This represents a significant improvement to the aerosol generator as this increases the amount of budesonide that is potentially respirable.

| Flow Passage | BUD deposition in spacer chamber | BUD MMAD |
| --- | --- | --- |
| Glass capillary (n = 11) | 24.6 (15.9) µg | 0.33 (0.1) µm |
| Stainless steel capillary (n = 4) | 0.7 (0.95) µg | 0.32 (0.1) µm |

The exact mechanism of the resultant altered solid component aerosol deposition following budesonide aerosol generation using the stainless steel flow passage versus a glass flow passage is unknown. While not wishing to be bound by theory, it is believed that there is a change in the electrostatic charge on the budesonide particles during aerosol generation using the glass and stainless steel flow passages, respectively, which results in less deposition in the spacer chamber when using a stainless steel flow passage.

3. Stainless Steel Sleeve

A stainless steel sleeve as described earlier herein was placed around the tip of a glass capillary flow passage from which an aerosol was emitted, forming an electrically conductive sleeve on the flow passage.

Comparative Examples A and B below were performed using a glass flow passage. Examples C and D were performed with the electrically conductive sleeve around the glass flow passage.

TABLE 1

| Example | Test solution | Experimental Apparatus | % on Capillary Holder | % in Throat | % in Impactor |
| --- | --- | --- | --- | --- | --- |
| Comparative Example A | 0.73% budesonide in propylene glycol | Cascade impactor | 24.1 (6.6) | 14.4 (9.5) | 61.5 (6.6) |
| Comparative Example B | 0.8% benzil in propylene glycol | Cascade impactor | 8.9 (6.2) | 26.7 (3.4) | 65.3 (8.8) |
| **Example C | 0.8% budesonide in propylene glycol | Cascade impactor | 0.4 (0.6) | 12.3 (7.9) | 87.2 (7.5) |
| **Example D | 0.8% budesonide in propylene glycol | Cascade impactor and spacer chamber* | 0.6 (0.5) | 24.9 (9.5) | 74.4 (9.7) |

*A large volume spacer chamber (6.3 L plexiglass box) was used to collect the aerosol prior to sampling into the Moudi cascade impactor.
**Sleeve present.

As can be seen from the above data (mean±SD deposition), the use of an electrically conductive metal sleeve around the sleeve of the glass flow passage significantly and reproducibly reduces the amount of material deposited in or on the aerosol generator itself (capillary holder), and greatly increases the amount of material delivered to the target site as represented by the impactor.

Spacer Chamber Tests

For the following examples, the CAG was run with a silica (glass) capillary flow passage. Statistical comparisons were made where appropriate using a paired t-test, as known in the art. Significance was assessed at the 95th percentile for probability. A minimum of five replicates of each experiment was performed and means (±standard deviation) are presented. The mass median aerodynamic diameter (D50)

was defined as the particle size at the 50th percentile on a cumulative percentage mass undersize distribution. In many cases, the MMAD was determined automatically by the Aerosizer Time-of-Flight Spectrometer (Amherst Process Instruments, Hadley, Mass.). In other cases, a cascade impactor was used as described elsewhere herein.

4. Effect of using a Large Volume Spacer Chamber on the Aerodynamic Particle Size Distribution of Aerosol 0.4% w/v benzil (BZ) dissolved in propylene glycol (PG) aerosols were produced, and drawn through the cascade impactor via two different entrance ports. The first was a plexiglass 90° USP throat (approx. volume 80 ml). This entrance port was used in control experiments. The second was a large volume plexiglass spacer chamber (approx. volume 6.3 L). Aerosol fired into the entrance ports was sized using the MOUDI cascade impactor (MSP Corporation, Minneapolis, Minn.) operating at 30 L/min. Five experiments were performed for both entrance ports. Particle size distributions were measured as the total mass distribution of propylene glycol and benzil, determined gravimetrically. The mass distribution of benzil alone was determined by HPLC.

Figures 5, 6:
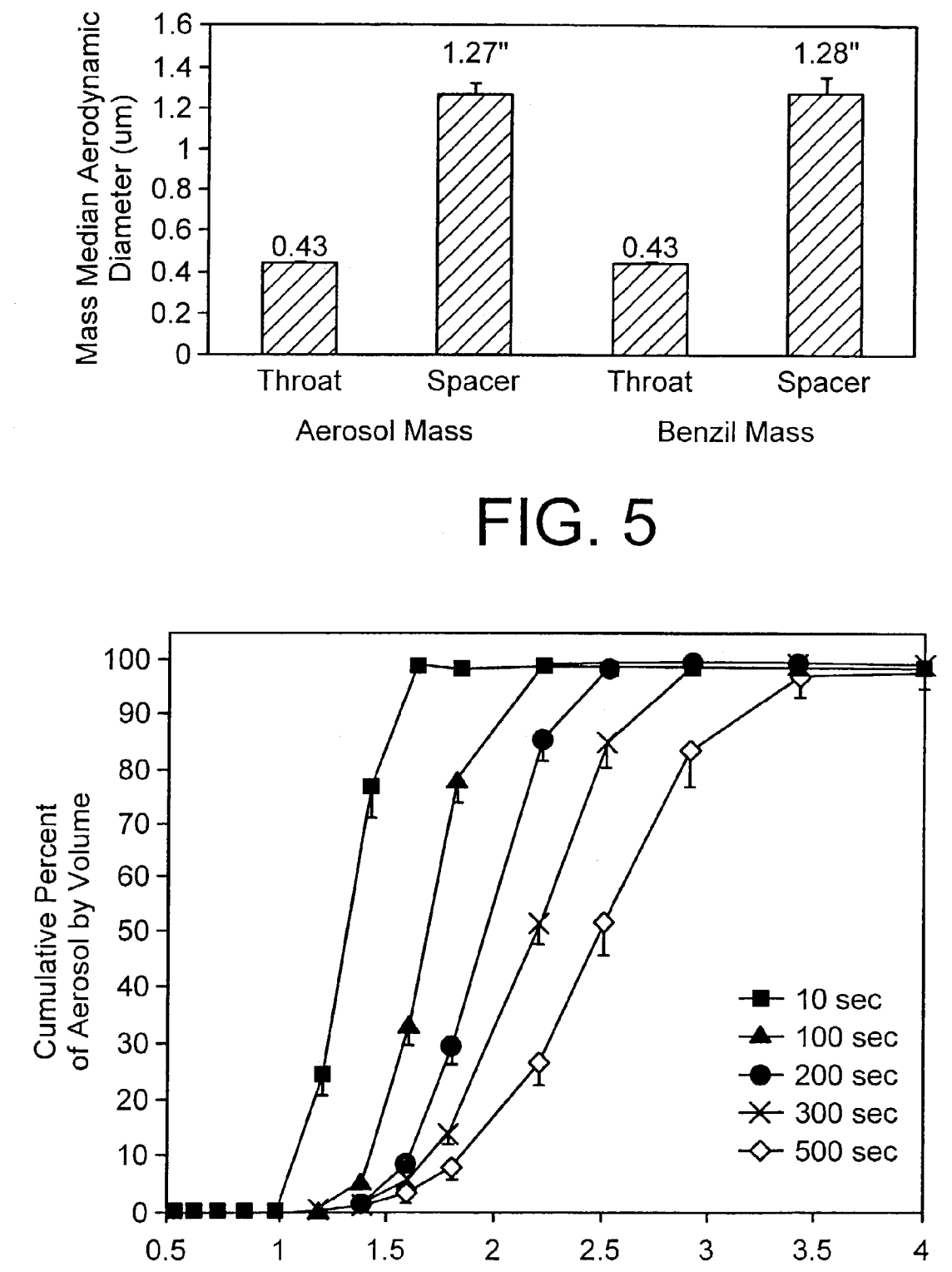

The results as shown in FIG. 5 demonstrate that use of the spacer chamber increased both the mean MMAD (error bars are SD) of the aerosol particles comprising aerosolized benzil and propylene glycol, as determined gravimetrically, and of the aerosolized benzil particles, as determined by HPLC assay.

5. Effect of Holding Time on the Aerosol Particle Size Distribution using a Large Volume Spacer Chamber (6.3L)

The effect of holding time on particle size distribution within a sealed spacer chamber was characterized using the Aerosizer Time-of-Flight Spectrometer (Amherst Process Instruments, Hadley, Mass.). Equivalent bolus amounts of propylene glycol were aerosolized and infused into a large volume plexiglass spacer chamber (approx. 6.3L) and sealed inside for durations of 10 sec., 100 sec., 200 sec., and 300 sec. Sampling into the Aerosizer was performed after these times. Five experiments were performed for each holding time.

Figure 7:
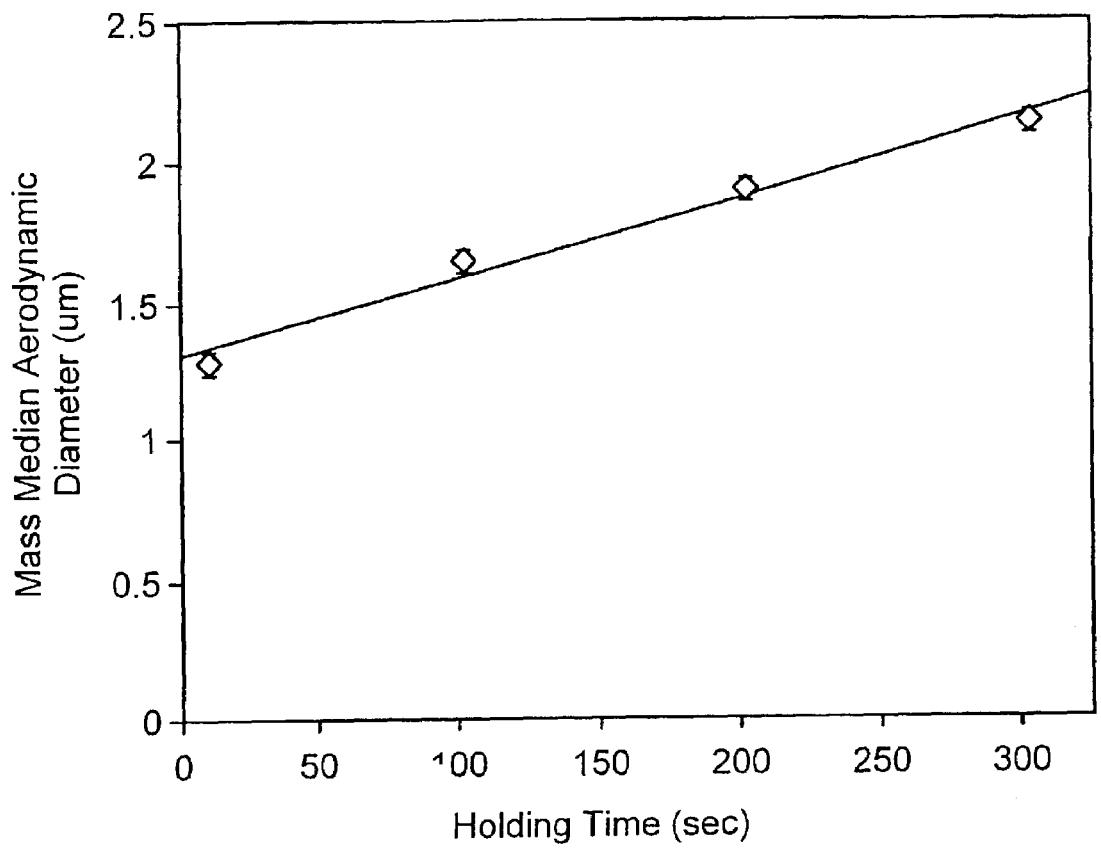
FIG. 7 is a second graph showing increase in particle size over time with use of a spacer chamber.

The results, as shown in FIGS. 6 and 7 (expressed as mean results±standard deviations), demonstrate the increase in MMAD of the particles over time.

6. Effect of Spacer Chamber Volume and Holding Time on the Aerodynamic Particle Size Distribution of CAG Aerosol A study was performed on the effect of spacer chamber volume on aerodynamic particle size distribution for propylene glycol aerosols with initially comparable aerodynamic size distribution and concentration. Glass conical spacer chambers of volumes 125 ml, 500 ml, 2000 ml and 6300 ml were used. Holding times of propylene glycol aerosol within the spacer chambers were 10 sec., 100 sec., 200 sec. and 300 sec. in duration prior to sizing. Five experiments were performed for each spacer chamber at each of the holding times. Sizing was again performed with the Aerosizer Time-of-Flight Spectrometer.

Figure 8:
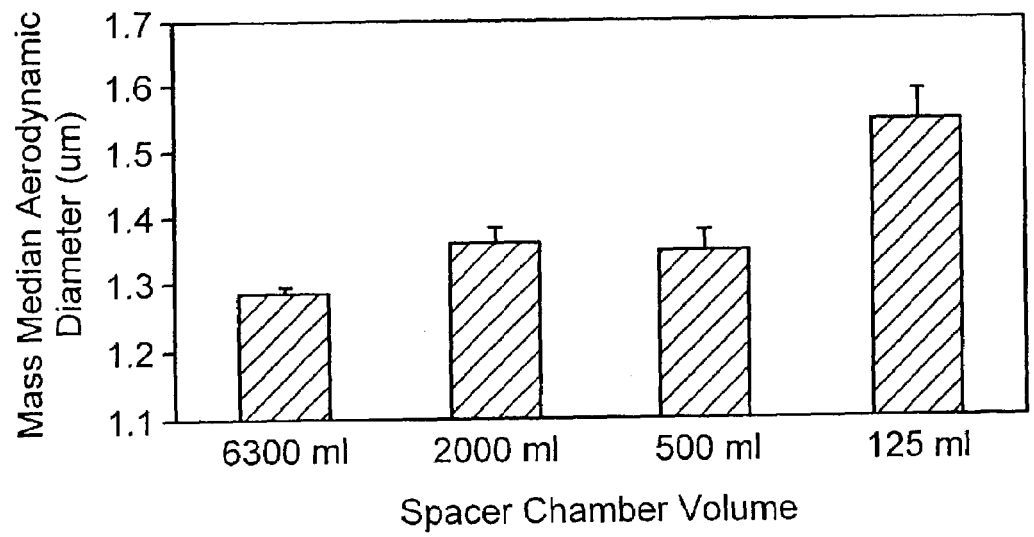
FIG. 8 is a graph showing increase in particle size with decreasing spacer chamber volume.
Figure 9:
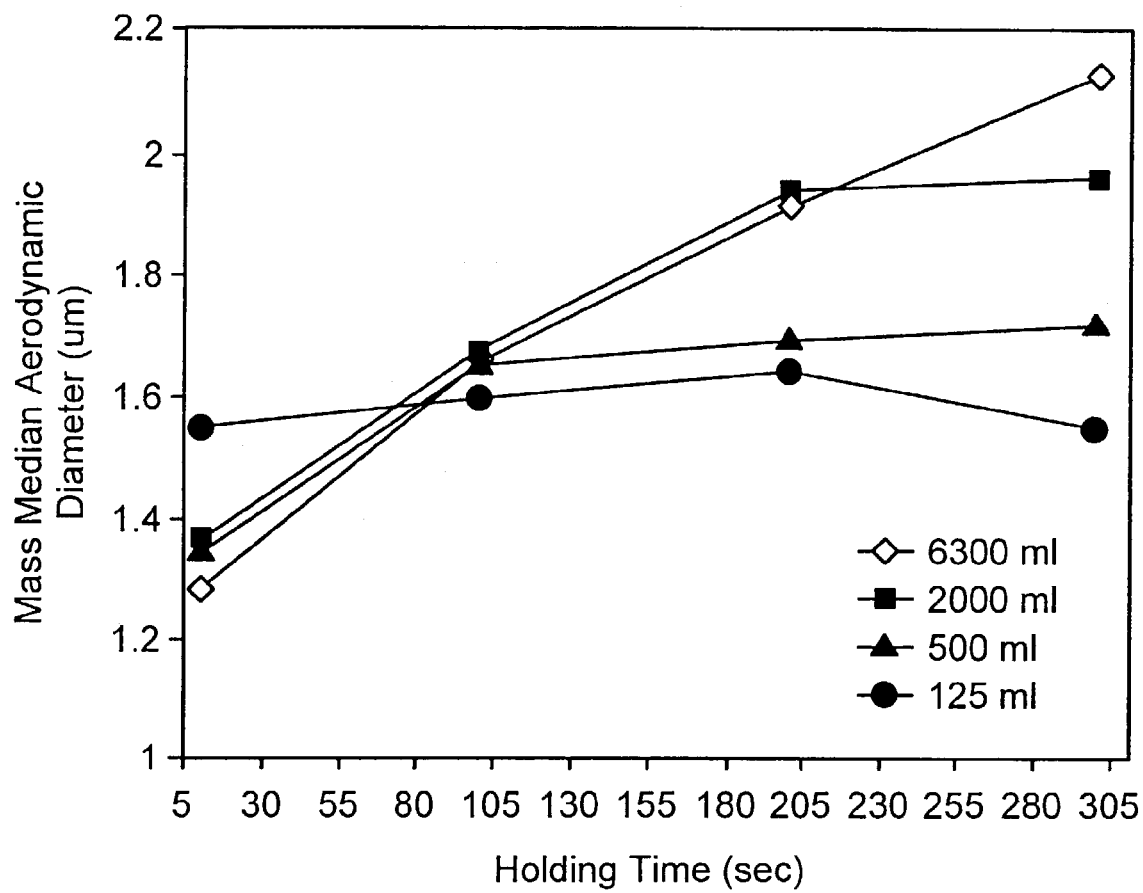
FIG. 9 is a graph showing the effects of holding time on the particle size of propylene glycol using spacers of various sizes.

The mean results (±SD) shown in FIG. 8 demonstrate the increase in MMAD of the particles with decreasing spacer chamber size, following a holding time of 10 sec. FIG. 9 reveals the effects of spacer chamber volume over a series of holding times. As shown in FIG. 9, holding time has little effect on small volume spacer chambers. However, there is a significant increase in MMAD as a function of holding time for larger spacer chambers, such as the 2000 ml and 6300 ml spacer chambers. It is observed that the change in particle size distribution lessens over time, suggesting a critical holding time beyond which the particle size does not change significantly for a given spacer chamber size.

7. Comparison of the Aerodynamic Particle Size Distribution of the Solid Component Particles of Budesonide and Benzil, and the Liquid Component, Propylene Glycol, when Aerosolized Table 2 shows the mass distribution of propylene glycol, budesonide and benzil when sampled via a throat (Comparative Example 1) and large volume (6.4L) Plexiglass spacer chamber without holding (Example 1), respectively, into a cascade impactor apparatus as shown in FIGS. 14A and B. A propylene glycol solution containing 0.4% budesonide and 0.4% benzil was aerosolized for this experiment.

Lower total mass recovery of propylene glycol reflected deposition within the spacer chamber. The MMAD of aerosolized propylene glycol and aerosolized benzil were identical when sampled via the throat (0.43 µm), however, the MMAD of aerosolized budesonide was significantly smaller (0.34 µm).

Using the spacer chamber, the aerosol particle size of propylene glycol and benzil was observed to increase. The MMAD of aerosolized PG and aerosolized benzil were nearly identical (1.27 µm and 1.28 µm, respectively), while the MMAD for the aerosolized budesonide particles was <0.2 µm.

In contrast to metered dose inhaler aerosols, which get smaller when fired through spacer chambers, aerosols generated by the CAG generally increased in particle size with respect to both the aerosolized solid component and aerosolized liquid component when sampled via a spacer chamber.

TABLE 2

| | PG | | BUD | | | | |
| --- | --- | --- | --- | --- | --- | --- | --- |
| | Total Mass Recovered | MMAD Total Mass | BUD Mass Total Recovered | BUD Mass Capillary Holder | BUD Mass Throat or Spacer | BUD Mass Impactor | MMAD BUD |
| Comparative Example 1 (Throat) | 24.98 mg | 0.43 µm | 65.2 µg | 12.8 µg | 14.3 µg | 38.3 µg | 0.34 µm |
| Example 1 (Spacer) | 17.04 mg | 1.27 µm | 65.8 µg | 22.1 µg | 12.4 µg | 31.3 µg | <0.2 µm |

TABLE 2-continued

| | BZ | | | | |
|---|---|---|---|---|---|
| | BZ Mass Total Recovered | BZ Mass Capillary Holder | BZ Mass Throat/ Spacer | BZ Mass Impactor | MMAD BZ |
| Comparative Example 1 (Throat) | 77.0 μg | 2.9 μg | 3.1 μg | 71.0 μg | 0.43 μm |
| Example 1 (Spacer) | 69.6 μg | 1.7 μg | 14.0 μg | 53.8 μg | 1.28 μm |

8. Characterization of the Effect of Spacer Chamber Volume on the In-Vitro Particle Size Distribution of Budesonide in a CAG Aerosol Table 3 summarizes the mass distribution of budesonide following aerosolization and sampling via a USP throat (Comparative Example) and sampling via glass spacer chambers with volumes of 2000 ml, 500 ml and 125 ml (Examples 1–3, respectively) using the following experimental conditions. A 0.75% budesonide in propylene glycol solution was aerosolized and sized using the Andersen cascade impactor, at a volumetric flow rate of 28.3 L/min. No holding time was employed in the throat studies, however a 10 sec. holding time was used for the spacer studies. Similar conditions and test solutions were used for each experiment. Budesonide concentration determinations were made by HPLC.

Experimental recovery of budesonide was comparable for each experiment, as shown in the columns labeled Total Mass Recovered and % Theoretical Recovery, with a range of 73.66–86.15% of the theoretical amount of budesonide being recovered. However, the regional distribution of budesonide was observed to vary throughout the apparatus as a function of (1) using a spacer chamber (compared to the throat) and (2) the volume of the spacer chamber used.

Figure 10:
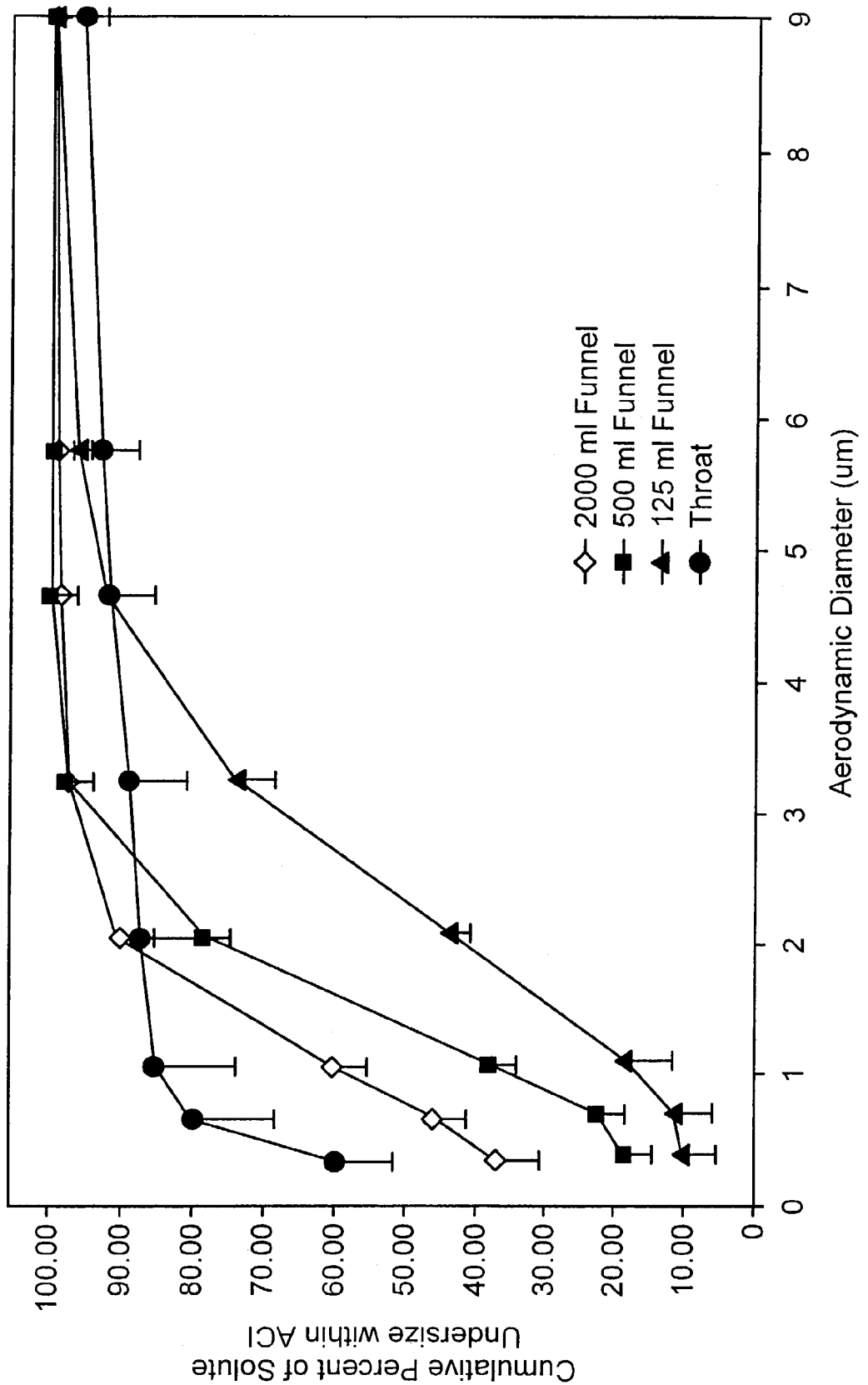
FIG. 10 is a graph showing increase in budesonide particle size with decreasing spacer chamber volume.

FIG. 10 shows the cumulative percent of solute undersize of budesonide found in the Comparative Example and Examples 1–3 of Table 3 versus the budesonide MMAD. The budesonide aerosol generated using the CAG and sampled via the throat contained about 60% of budesonide particles that were less than 0.4 μm (Comparative Example). This is an extremely high fraction of sub-micron particles. Following aerosol generation into the 2000 ml spacer chamber, the measured mass of particles less than 0.4 μm was reduced to about 38% of the sampled aerosol (Example 1).

Further reduction in spacer chamber size further reduced the fraction of sub-micron particles available for inhalation (500 ml=19% (Example 2); 125 ml=11% (Example 3)). This change in budesonide aerosol particle size distribution is reflected in the MMAD for these aerosols as shown in Table 3.

The MMAD of the budesonide aerosol sampled via the throat could not be accurately determined using the Andersen cascade impactor. It was shown to be less than 0.4 μm. (Previous studies using an alternative impactor, the MOUDI, have revealed a MMAD for budesonide sampled via the throat of approximately 0.2–0.3 μm. The MMAD of budesonide following aerosolization via the 2000, 500 and 125 ml spacer chambers was 0.81 μm, 1.40 μm and 2.37 μm, respectively.

These experiments indicate that appropriate selection of a spacer chamber volume allows the particle size distribution of the solid component (budesonide) and liquid component (propylene glycol) to be manipulated. Those skilled in the art will also recognize that different spacer chamber shapes as well as volumes may influence these results further. This allows aerosols of various particle size distributions to be produced to target regional deposition of medicaments within the lung by using a combination of the CAG and a suitable spacer chamber volume and design.

TABLE 3

| | BUDESONIDE | | | | | | | | |
|---|---|---|---|---|---|---|---|---|---|
| | Total Mass Recovered (μg) | Mass in Impactor (μg) | Mass in Spacer or Throat (μg) | Mass in Capillary Holder (μg) | MMAD (μm) | Impactor % of Total | Throat or Spacer Chamber % of Total | Capillary Holder % of Total | % Theoretical Recovery |
| Comparative Throat Example | 181.63 | 155.72 | 24.65 | 1.22 | <0.4 | 85.47 | 13.81 | 0.69 | 86.15 |
| Example 1 2000 ml | 162.95 | 116.78 | 41.19 | 4.82 | 0.81 | 71.85 | 24.87 | 3.20 | 77.29 |
| Example 2 500 ml | 155.29 | 102.55 | 43.54 | 9.21 | 1.40 | 66.64 | 28.23 | 5.13 | 73.66 |
| Example 3 125 ml | 164.27 | 66.88 | 94.40 | 2.55 | 2.37 | 40.98 | 57.20 | 1.55 | 77.92 |

The results of Table 3 are shown graphically in FIG. 10.

Solvent Tests

9. The Following Examples were Performed using a Silica Capillary Flow Passage.

Preliminary aerosol generation studies using benzil as a model solute (solid or liquid component) dissolved in a propylene glycol vehicle and generated as an aerosol using the CAG revealed a pattern of co-evaporation and co-condensation of solute and vehicle. The phenomenon called co-condensation is defined as indicating that the aerodynamic particle size distribution of the vehicle and solute are identical when collected and measured using a cascade impaction method. The total mass distribution of the aerosol determined gravimetrically can essentially be considered to be the vehicle distribution because the vehicle represents 99.6% of the aerosol mass. The distribution of the solute was determined by specific chemical analysis.

Figure 11:
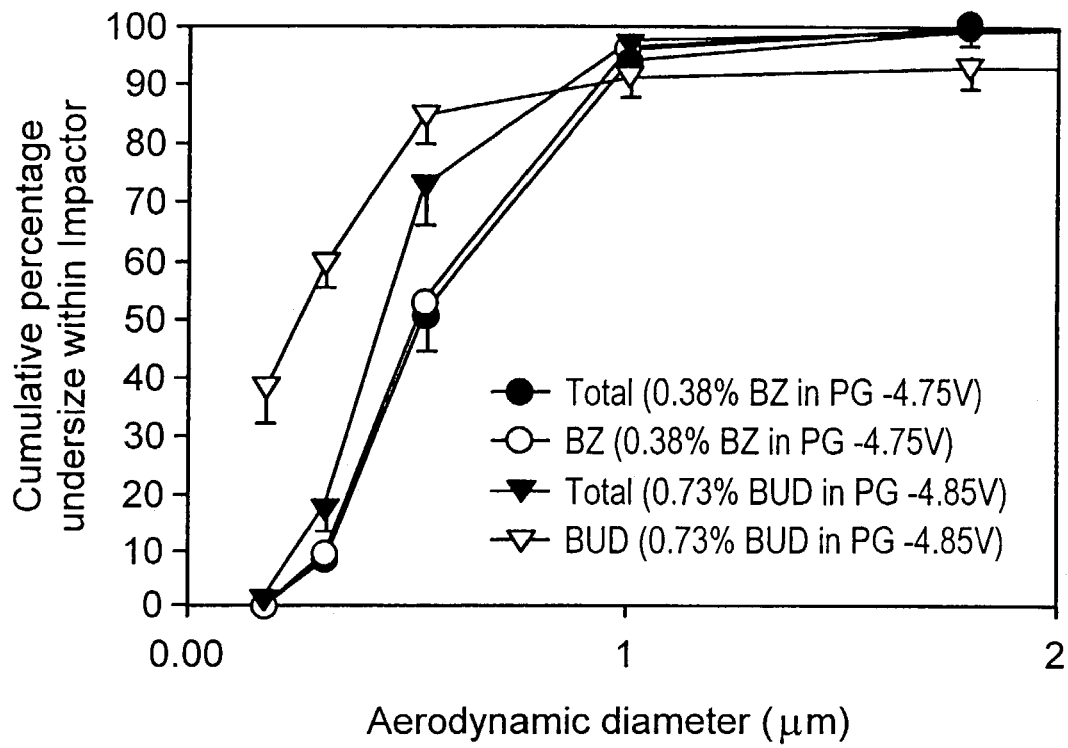
FIG. 11 is a graph of particle size following aerosol generation from solutions of benzil in propylene glycol, and budesonide in propylene glycol, respectively.

FIG. 11 shows the mean aerodynamic particle size distributions of BZ, BUD and PG (error bars are standard deviation) following aerosolization using a CAG. The solution compositions are indicated in FIG. 11. Co-condensation of vehicle and solute are observed for BZ in PG, but not for BUD in PG. Table 4 shows the mean mass median aerodynamic diameters (with standard deviation) of both the total aerosol and the solute component for the benzil and budesonide aerosols, respectively.

In an attempt to investigate the mechanism whereby benzil co-condenses with PG and budesonide does not, an experiment was performed using a test formulation containing 0.4% w/v of each solute. Table 4 reveals that when a mixed solute system, i.e., a system with more than one dissolved component, is aerosolized, the characteristics of condensation of the individual solutes were unaltered. That is, benzil co-condensed with propylene glycol, while budesonide was observed to have a significantly lower MMAD compared to the propylene glycol vehicle.

Figure 12:
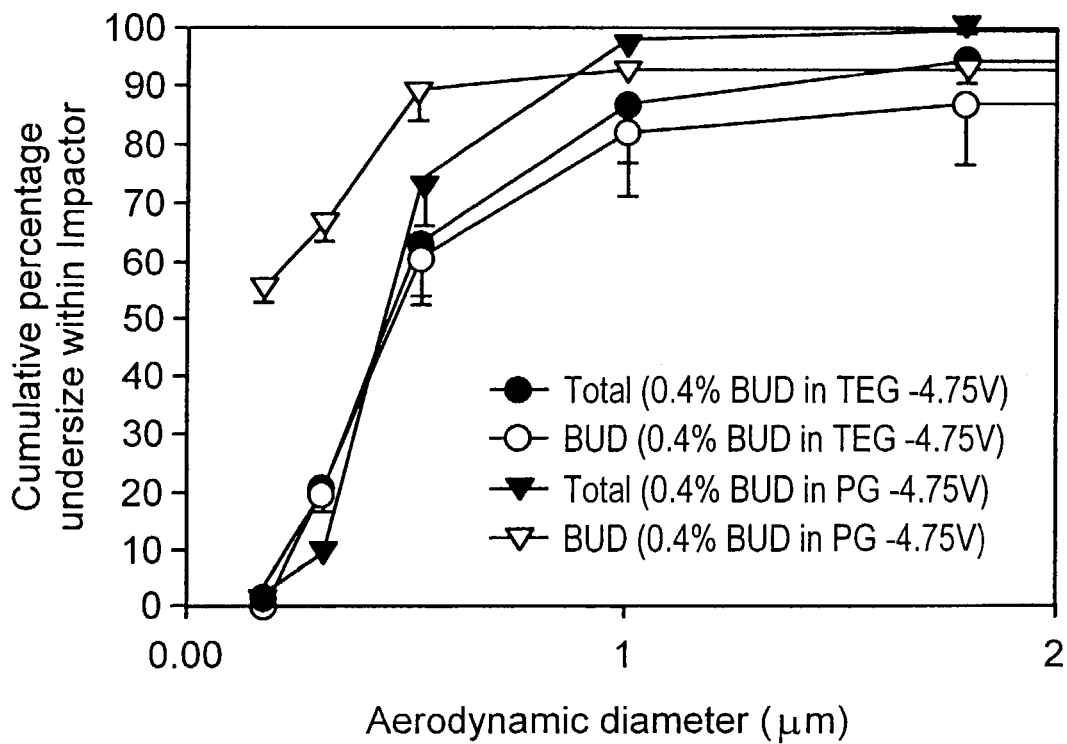
FIG. 12 is a graph of particle size following aerosol generation from solutions of budesonide in propylene glycol and budesonide in triethylene glycol.
Figure 13A:
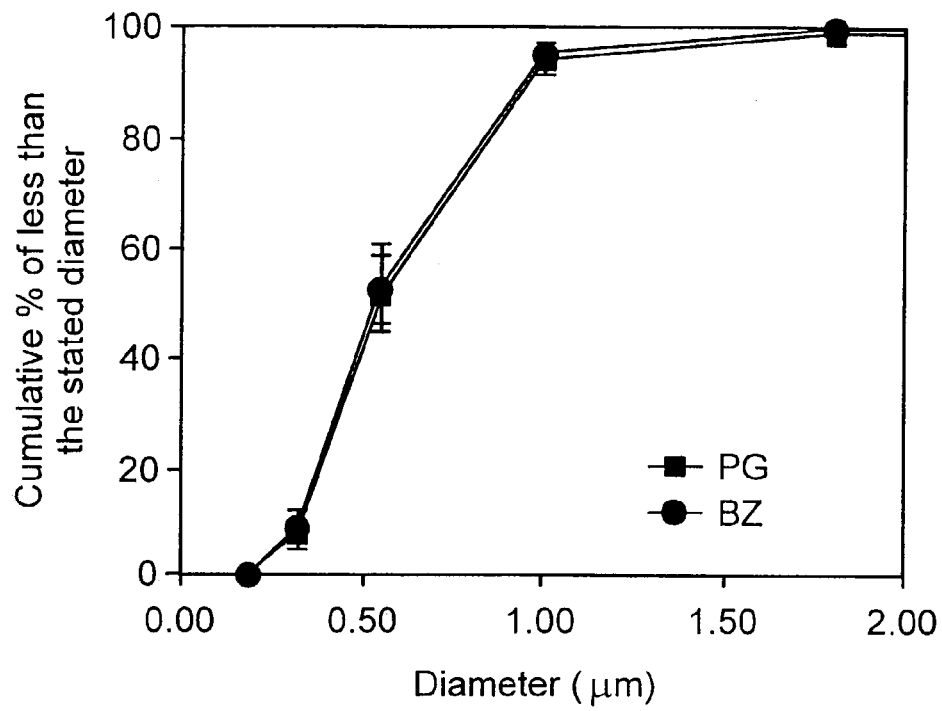
FIGS. 13(a)–(d) are graphs depicting particle size of aerosols from (a) benzil in propylene glycol, (b) benzil in triethylene glycol, (c) budesonide in propylene glycol, and (d) budesonide in triethylene glycol.
Figure 13B:
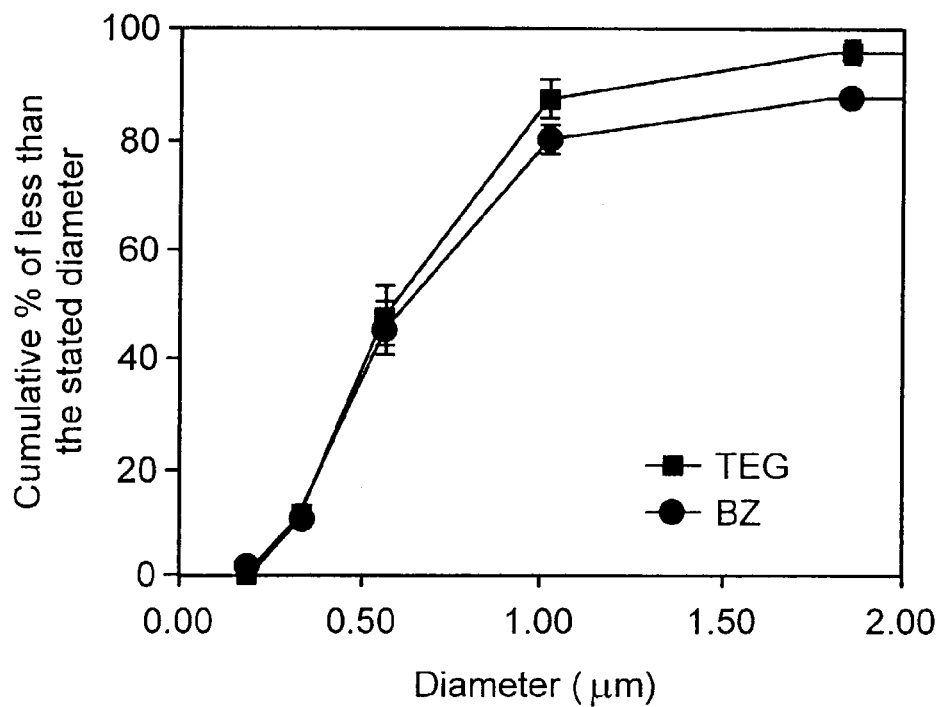
Figure 13C:
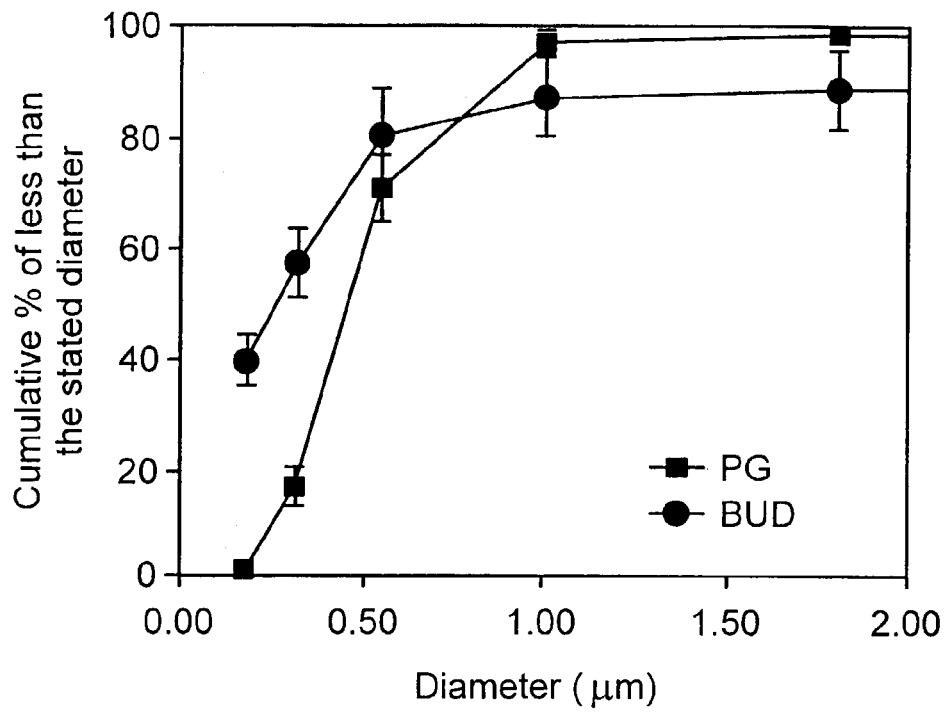
Figure 13D:
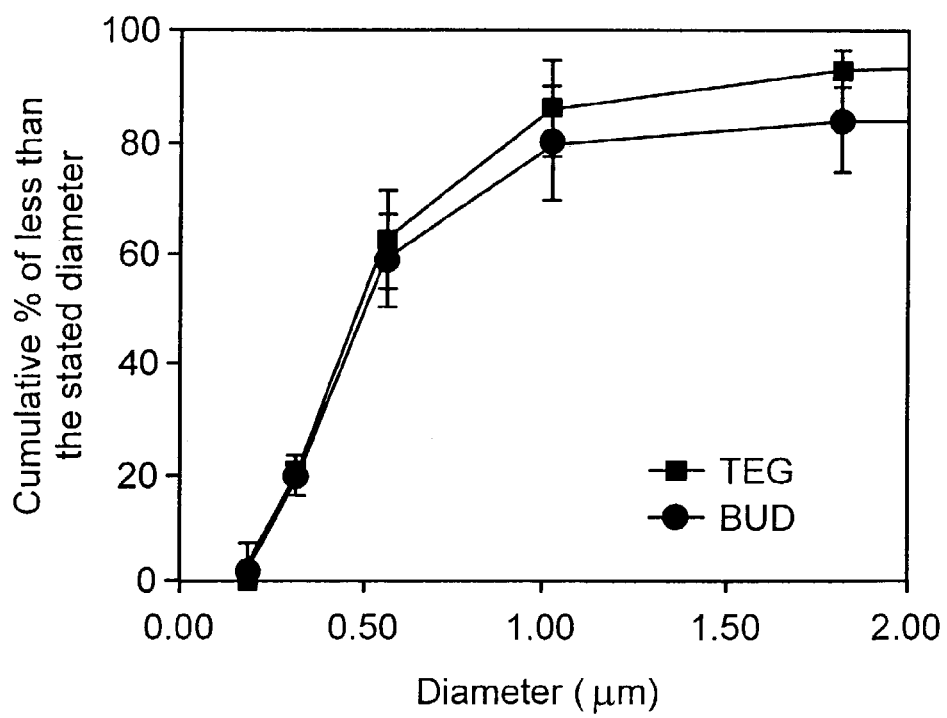

As an alternative to propylene glycol, the aerosol characteristics of budesonide and benzil solid component aerosols in triethylene glycol (TEG) was tested. Table 4 reveals that there was no significant difference between the total aerosol MMAD and the solute MMAD following aerosolization of benzil or budesonide in triethylene glycol. Co-condensation occurred with both solutes. FIG. 12 compares the mean aerodynamic particle size distribution (error bars are standard deviation) of a 0.40% w/v budesonide in triethylene glycol solution and a 0.40% w/v budesonide in propylene glycol solution following aerosolization using the CAG. Co-condensation of budesonide and vehicle was only observed when budesonide was aerosolized in a triethylene glycol vehicle.

TABLE 4

| Formulation | Total MMAD in μm (Standard Deviation) | Solute component MMAD in μm (Standard Deviation) | |
|---|---|---|---|
| 0.38% w/v Benzil in PG | 0.54 (0.05) | 0.54 (0.05) | |
| 0.73% w/v Budesonide in PG | 0.46 (0.02) | 0.27 (0.05) | |
| 0.4% w/v Benzil and 0.4% Budesonide in PG | 0.43 (0.01) | Benzil 0.43 (0.01) | Budesonide 0.34 (0.02) |
| 0.4% w/w Benzil in TEG | 0.57 (0.05) | 0.61 (0.05) | |
| 0.4% w/w Budesonide in TEG | 0.49 (0.06) | 0.50 (0.05) | |

A preferred embodiment of some CAG aerosols may require co-condensation of the solute and the vehicle to minimize exhalation of the resultant sub-micron particles. If the solute, after aerosolization, is significantly smaller than the aerosolized liquid component, the aerosolized solute may separate from the liquid component and be expelled from the patient's lungs before settling in the target area. Thus, the desired medicament in the form of the aerosolized solute would not be administered in the proper location, or in the desired amount, to the patient. Alternatively, if the solute after aerosolization is larger than the liquid component, the solute may settle too soon in the lungs or settle in the back of the mouth or throat of the patient, or in the aerosol generator, thus diminishing medicament delivery. The use of triethylene glycol as a vehicle is one mechanism by which the co-condensation of budesonide aerosols can be effected, thereby preventing these problems.

Further data regarding the co-condensation, or lack thereof, of budesonide and benzil in propylene glycol and triethylene glycol is shown in FIGS. 13 (a–d). It is clear from this figure that aerosolized benzil has approximately the same MMAD as both aerosolized propylene glycol and aerosolized triethylene glycol (FIG. 13(a), FIG. 13(b)), while aerosolized budesonide has approximately the same MMAD as aerosolized triethylene glycol (FIG. 13(d)), but not propylene glycol (FIG. 13(c)).

Those skilled in the art will recognize that some medicaments may benefit from CAG aerosolization and inhalation without co-condensation with the vehicle. For example, aerodynamic particle sizes substantially less than 0.5 μm, such as about 0.1 or 0.2 μm, are known to be deposited homogeneously by aerosol particle diffusion in the extreme lung periphery. It is feasible that some medicaments when deposited in such very small sizes from aerosols having vehicles with a greater MMAD may exhibit substantially different pharmaceutical and pharmacological or toxicological properties than medicaments with a MMAD similar to those of the vehicle.

While this invention has been illustrated and described in accordance with preferred embodiments, it is recognized that variations and changes may be made without departing from the invention as set forth in the claims.

What is claimed is:

1. A method of generating an aerosol containing budesonide, comprising:
   supplying a liquid containing a suspension of propylene glycol and particles consisting essentially of budesonide to a flow passage;
   heating the liquid in the flow passage such that the liquid is volatilized and expands out of an open end of the flow passage and forms a propylene glycol aerosol of aerosolized budesonide having a mass median aerosol diameter (MMAD) of 2 μm or less, wherein the liquid includes propylene glycol and the aerosol includes aerosolized propylene glycol having a larger MMAD than the aerosolized budesonide.

2. The method of claim 1, wherein the flow passage is an electrically conductive flow passage and the heating is carried out by passing electrical current through the electrically conductive flow passage.

3. The method of claim 1, wherein the liquid is supplied from a source which creates a back pressure of at least 20 psi while the liquid is heated.

4. The method of claim 1, wherein the flow passage is a capillary passage.

5. The method of claim 1, wherein the liquid is supplied continuously to the flow passage.

6. The method of claim 1, wherein the heating occurs upon breath-actuation of a hand-held inhaler incorporating the flow passage therein.

7. The method of claim 1, wherein the aerosol is formed in a mouthpiece of a hand-held inhaler.

8. The method of claim 1, wherein the aerosol is formed by condensation of the volatilized liquid.

9. The method of claim 1, wherein the aerosol is formed in a spacer chamber of a hand-held inhaler.

10. The method of claim 1, wherein the flow passage includes an electrically conductive sleeve at the open end, the conductive sleeve being effective to provide a narrow particle size distribution of the aerosol.

11. The method of claim 1, wherein the liquid is supplied to the flow passage at a rate of at least 1 milligram/second.

12. The method of claim 1, wherein the liquid consists of solid budesonide particles suspended in propylene glycol.

13. The method of claim 1, wherein the method results in a theoretical recovery of at least about 73%.

* * * * *